(12) United States Patent
Noda et al.

(10) Patent No.: US 10,502,752 B2
(45) Date of Patent: Dec. 10, 2019

(54) REACTION METHOD INCLUDING PIPETTE HEIGHT DETECTION AND CORRECTION

(71) Applicant: Konica Minolta, Inc., Chiyoda-ku, Tokyo (JP)

(72) Inventors: Tetsuya Noda, Hino (JP); Masataka Matsuo, Hachioji (JP); Youichi Aoki, Toda (JP)

(73) Assignee: Konica Minolta, Inc., Chiyoda-ku, Tokyo (JP)

( * ) Notice: Subject to any disclaimer, the term of this patent is extended or adjusted under 35 U.S.C. 154(b) by 93 days.

(21) Appl. No.: 15/772,558

(22) PCT Filed: Oct. 27, 2016

(86) PCT No.: PCT/JP2016/081891
§ 371 (c)(1),
(2) Date: May 1, 2018

(87) PCT Pub. No.: WO2017/082069
PCT Pub. Date: May 18, 2017

(65) Prior Publication Data
US 2019/0091679 A1 Mar. 28, 2019

(30) Foreign Application Priority Data
Nov. 13, 2015 (JP) .................................. 2015-223436

(51) Int. Cl.
*G01N 35/10* (2006.01)
*B01L 3/02* (2006.01)

(52) U.S. Cl.
CPC ........ *G01N 35/1011* (2013.01); *B01L 3/0237* (2013.01)

(58) Field of Classification Search
CPC .............. G01N 35/1011; B01L 3/0237; B01L 2200/146; B01L 2200/148
See application file for complete search history.

(56) References Cited

U.S. PATENT DOCUMENTS 5,133,392 A * 7/1992 Hamann ............... B01L 3/0262
141/1
7,823,535 B2 * 11/2010 Hanafusa .............. B01L 3/0268
118/665

(Continued)

FOREIGN PATENT DOCUMENTS

| JP | 2013024607 | 2/2013 |
| WO | 2011152064 | 12/2011 |

OTHER PUBLICATIONS

International Search Report issued in parent PCT Application No. PCT/JP2016/081891, dated Jan. 24, 2017.

*Primary Examiner* — Justin N Olamit
(74) *Attorney, Agent, or Firm* — Baker Hostetler

(57) ABSTRACT

A reaction method includes a reaction step of reacting two or more substances with each other by using a pipette tip, attached to a pipette nozzle, for sucking or discharging a liquid to supply a liquid to a reaction field and remove the liquid from the reaction field a plurality of times. The reaction method further includes: a first process of, prior to the reaction step, detecting an end height of the pipette tip and setting a reference height of the pipette nozzle on the basis of the end height of the pipette tip; and a second process of correcting, in a course of the reaction step, the height of the pipette nozzle from the reference height so as to cancel out variation in the end height of the pipette tip due to a change in the temperature of the pipette tip.

20 Claims, 10 Drawing Sheets

(56) References Cited

U.S. PATENT DOCUMENTS

| | | | |
|---|---|---|---|
| 8,765,079 B2* | 7/2014 | Tokumaru | C12M 23/10 422/509 |
| 9,745,612 B2* | 8/2017 | Decaux | C12Q 1/24 |
| 9,878,322 B2* | 1/2018 | Hutter | B01L 3/021 |

* cited by examiner

REACTION METHOD INCLUDING PIPETTE HEIGHT DETECTION AND CORRECTION

CROSS-REFERENCE TO PRIOR APPLICATIONS

This application is a 371 national stage application of PCT/JP2016/081891 filed Oct. 27, 2016 and claims priority to JP 2015-223436, filed Nov. 13, 2015, the entire disclosures of which are referenced herein in their entirety.

TECHNICAL FIELD

The present invention relates to a reaction method including a reaction step of reacting two or more substances with each other using a pipette tip, attached to a pipette nozzle, for aspirating or discharging a liquid.

BACKGROUND ART

By enabling a clinical test or the like to detect a trace amount of a detection target substance, such as protein or DNA, quantitatively with high sensitivity, it is possible to rapidly grasp conditions of a patient at the time of treatment. Therefore, there is a need for a method and apparatus capable of quantitatively detecting a trace amount of a detection target substance with high sensitivity. As a method capable of detecting a detection target substance with high sensitivity, there is a known method of a surface plasmon-field enhanced fluorescence spectroscopy (hereinafter abbreviated as "SPFS") (refer to Patent Literature 1).

The surface plasmon-field enhanced fluorescence analysis method described in Patent Literature 1 includes: a step of applying excitation light to a prism on which a metal thin film is formed so as to allow the excitation light to be totally reflected on the metal thin film and then measuring plasmon scattered light generated on a surface of the metal thin film as a result of total reflection of the excitation light on the metal thin film; a step of determining an incident angle (enhancement angle) maximizing the intensity of the measured plasmon scattered light as the incident angle of the excitation light with respect to the metal thin film; a reaction step of supplying a second capture agent (for example, a secondary antibody) labeled with a detection target substance and a fluorescent substance onto a metal thin film on which a first capture agent (for example, a primary antibody) capable of specifically binding to a detection target substance is immobilized; and a detection step of emitting the excitation light with the determined enhancement angle and then measuring the fluorescence intensity of the fluorescence emitted from the fluorescent substance labeling the detection target substance on the metal thin film.

In the surface plasmon-field enhanced fluorescence analysis method described in Patent Literature 1, the detection target substance binds to the first capture agent when a liquid specimen containing the detection target substance is supplied onto the metal thin film. Subsequently, the detection target substance is labeled with the fluorescent substance when a labeling liquid containing the second capture agent labeled with the fluorescent substance is supplied onto the metal thin film to which the detection target substance is bound. When the excitation light is applied to the metal thin film in this state, the fluorescent substance labeling the detection target substance is excited by an electric field enhanced by surface plasmon resonance (hereinafter abbreviated as "SPR") and releases fluorescence. Accordingly, the fluorescence emitted from the fluorescent substance is detected to enable detection of the presence or amount of the detection target substance.

In order to detect a trace amount of the detection target substance quantitatively with high sensitivity in this manner, there is a need to supply and remove the specimen and the labeling liquid with high accuracy. Generally, specimens and labeling liquids are supplied and removed using a pipette tip. In addition, since the pipette tips are integrally formed by injection molding or the like, their lengths are different from each other. There is a known method of supplying and removing the specimen or the labeling liquid in consideration of different lengths of pipette tips (for example, refer to Patent Literature 2).

The method of supplying and removing a liquid described in Patent Literature 2 uses a photosensor to detect an end position of a pipette tip formed of resin attached to a pipette nozzle. Then, the position of the pipette nozzle is adjusted on the basis of information indicating the end position of the pipette tip so as to supply and remove the liquid with high accuracy.

CITATION LIST

Patent Literature

Patent Literature 1: WO 2011/152064 A
Patent Literature 2: JP 2006-275820 A

SUMMARY OF INVENTION

Technical Problem

Reaction for allowing the trace amount of a detection target substance to be captured by a capture agent or the like as described above exhibits variable reactivities depending on the reaction temperature. Therefore, the apparatus manages a reaction section inside the apparatus at a constant temperature optimum for the reaction regardless of the installation environment temperature of the apparatus. In contrast, the pipette tip supplied to the apparatus is arranged in a temperature environment such as room temperature, different from the environment of the reaction section within the apparatus, unless the pipette installed in the apparatus beforehand. This causes the total length of the pipette tip to change depending on the ambient temperature at the time of supply and removal when the pipette tip is supplied to the apparatus at the time of measurement.

Meanwhile, a liquid delivery method described in Patent Literature 2 has little consideration of the environmental temperature at the time of supply and removal, leading to a change in the end height of the pipette tip with time and a failure in supply and removal of the liquid with high accuracy in some cases. In particular, high-accuracy control of the end height of the pipette tip is difficult when precise control of the reaction step is desired, leading to problems of failing to manage the residual liquid amount after removal of the liquid with high accuracy and causing a state in which the end of the pipette tip comes in contact with the bottom surface of the flow path.

In view of the above, the present invention aims to provide a reaction method capable of controlling the end height of a pipette tip with respect to a reaction field with high accuracy even when the pipette tip is influenced by the temperature and of appropriately reacting two or more substances with each other in the reaction field.

Solution to Problem

In order to solve the above-described problems, a reaction method according to an embodiment of the present invention is a reaction method including a reaction step of reacting two or more substances with each other by using a pipette tip, attached to a pipette nozzle, for sucking or discharging a liquid to supply a liquid to a reaction field and remove the liquid from the reaction field a plurality of times, the reaction method including: a first process of, prior to the reaction step, detecting an end height of the pipette tip and setting a reference height of the pipette nozzle on the basis of the end height of the pipette tip; and a second process of correcting, in a course of the reaction step, the height of the pipette nozzle from the reference height so as to cancel out variation in the end height of the pipette tip due to a change in the temperature of the pipette tip.

Advantageous Effects of Invention

According to the present invention, the end height of the pipette tip can be controlled with high accuracy even when the pipette tip expands or contracts due to a change in the temperature of the pipette tip. This enables the control of the amount of liquid in the reaction field with high accuracy. According to the present invention, the presence or amount of a detection target substance can be detected with high accuracy, for example.

DESCRIPTION OF EMBODIMENTS

Hereinafter, an embodiment of the present invention will be described in detail with reference to the drawings. A reaction method according to an embodiment of the present invention includes a reaction step of reacting two or more substances with each other by using a pipette tip, attached to a pipette nozzle, for sucking or discharging a liquid to supply the liquid to a reaction field and remove the liquid from the reaction field a plurality of times.

First Embodiment

Figure 1:
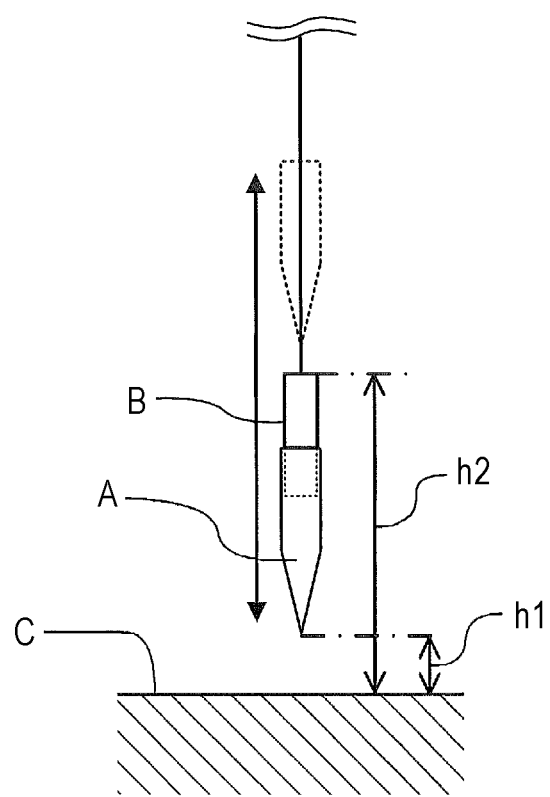
FIG. 1 is a diagram for illustrating a first process of a reaction method according to a first embodiment.
Figure 2A:
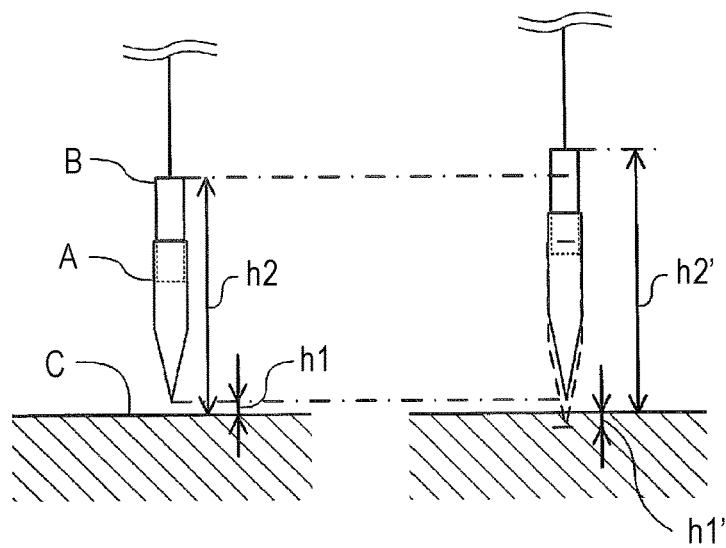
FIGS. 2A and 2B are diagrams for illustrating a second process of the reaction method according to the first embodiment.
Figure 2B:
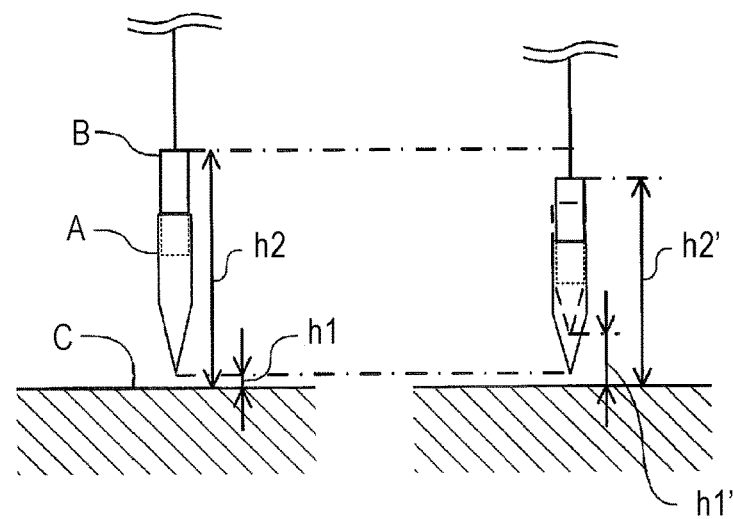

FIGS. 1 and 2 are diagrams for illustrating a reaction method according to a first embodiment of the present invention. FIG. 1 is a diagram illustrating a step (in first process) of detecting an end height of a pipette tip A. FIG. 2 is a diagram illustrating a step (in second process) of setting a reference height of a pipette nozzle B. FIG. 2A is a diagram for illustrating a case where the temperature at which the pipette tip A is attached to the pipette nozzle B is lower than the temperature at which the reaction step is performed. FIG. 2B is a diagram for illustrating a case where the temperature at which the pipette tip A is attached to the pipette nozzle B is higher than the temperature at which the reaction step is performed.

The reaction method according to the first embodiment is a method in which the temperature of the pipette tip A is not measured. The reaction method includes a first process of setting the reference height of the pipette nozzle B before the reaction step and a second process of correcting the height of the pipette nozzle B from the reference height in the course of the reaction step. Note that the "reaction step" is a step including operation of supplying a liquid to a reaction field and operation of removing the liquid from the reaction field, and specifically includes a step of supplying a specimen to the reaction field then reacting two or more substances with each other and thereafter removing the specimen, and a step of supplying a washing liquid to the reaction field and then removing the washing liquid from the reaction field. Note that a "liquid" includes a specimen, a washing liquid, a buffer solution. The reaction method according to the present embodiment is applicable to cases where there is a difference between a temperature (first temperature) of the pipette tip in the first process of attaching the pipette tip A to the pipette nozzle B and a temperature (second temperature) of the pipette tip in the reaction step of reacting two or more substances with each other. Note that the first temperature may be higher than the second temperature or lower than the second temperature. Herein, a case where the first temperature is lower than the second temperature will be described. An exemplary case where the first temperature is lower than the second temperature is a case where the apparatus is installed in a temperature environment of 20° C. (normal temperature) while the temperature of the portion of the apparatus performing the reaction step is controlled at 37° C. There is a case where the pipette tip A stored in a temperature environment of 20° C. (normal temperature) may be installed onto the apparatus by opening a hatch (not illustrated) of the apparatus.

In the step (in first process) of attaching the pipette tip A to the pipette nozzle B and detecting the end height of the pipette tip A, the elapsed time after installation of the pipette tip A in the apparatus is short. Therefore, the temperature of the pipette tip A has not increased so much, and it is still about 20° C., for example, and after a predetermined time elapses, the temperature of the pipette tip A gradually increases influenced by the internal temperature of portions around the pipette tip A. The temperature of the pipette tip A in the reaction step is the temperature (about 20° C.) in the first process or above, and might rise up to 37° C.

Herein, as an example involving the temperature change of the pipette tip A, the internal temperature at which the reaction step is performed is held at 37° C. The example described herein is a case where the apparatus and the pipette tip A are installed in a temperature environment lower than the internal temperature and the pipette tip A having an initial temperature lower than the internal temperature is brought into the apparatus. At this time, there is a case where opening and closing of the hatch of the apparatus causes the outside air to flow into the apparatus, and the internal temperature around the pipette nozzle B temporarily changes in a direction to approach the outside air temperature at the point of installation of the pipette tip A (point of the subsequent first process).

As another example, there is a case where the space in which the pipette tip A is attached to the pipette nozzle B and the space in which the reaction step is performed are separate spaces in the apparatus, and the space in which the reaction is performed is selectively managed at 37° C. while the attachment space is not temperature-controlled (for example, the temperature is close to the outside air temperature at which the apparatus is installed).

As illustrated in FIG. 2, prior to the reaction step, the first process detects the end height of the pipette tip A, and sets the reference height of the pipette nozzle B on the basis of the end height of the pipette tip A. A method of detecting the end height of the pipette tip A is not particularly limited. An exemplary method for detecting the end height of the pipette tip A includes a method of using an air pressure in the pipette tip A. This is a method of measuring a change in the air pressure within the pipette tip A when a gas is sucked or discharged from the end of the pipette tip A with varied intervals between the end of the pipette tip A and a reference portion (reaction field in the present embodiment) C being the reference height of the end of the pipette tip A. More specifically, first, in a state where the end of the pipette tip A and the reference portion (reaction field) C are separated from each other, a first pressure within the pipette tip A when the gas is sucked or discharged from the end of the pipette tip A is measured. Subsequently, in a state where the end of the pipette tip A and the reference portion C are closer to each other than in the measurement of the first pressure, a second pressure within the pipette tip A when the gas is sucked or discharged from the end of the pipette tip A is measured. Finally, the end height of the pipette tip A with respect to the reference portion is detected on the basis of a difference between the first pressure and the second pressure.

Next, a reference height (h2) of the pipette nozzle A is set on the basis of the end height of the pipette tip A. As illustrated in the left diagram of FIG. 2A, the present embodiment corrects the detected end height of the pipette tip A to a height h1 (100 µm, for example) at which the liquid is removed from the reaction field. The corrected height of the pipette nozzle B is the reference height (h2) of the pipette nozzle B.

In the second process, as illustrated in the right diagram of FIG. 2A, the height of the pipette nozzle B is corrected from the reference height in the course of the reaction step so as to cancel out the variation of the end position of the pipette tip A due to the change in the temperature of the pipette tip A.

With the elapsed time after the first process, the end height of the pipette tip A varies to approach the reaction field. In the present embodiment, the end height of the pipette tip A varies from h1 to h1'. This is because the internal temperature around the pipette tip A is higher than the temperature at the time of installation of the pipette tip A in the apparatus, and thus, the temperature of the pipette tip A gradually increases with the internal temperature, resulting in an increase of the total length of the pipette tip A. In a case where the reaction step is allowed to proceed as it is, the end of the pipette tip A would come into contact with the reaction field, making it difficult to properly remove the liquid from the reaction field.

To cope with this, the height of the pipette nozzle B is corrected from the reference height h2 to h2' so as to cancel out the variation of the end height of the pipette tip A. That is, the height of the pipette nozzle B is corrected to make it higher with respect to the reaction field so as to set the end of the pipette tip A with respect to the reaction field to be at the predetermined height (h1).

Note that in a case where the internal temperature around the pipette tip A is lower than the temperature at the time of installation of the pipette tip A in the apparatus, the total length of the pipette tip A gradually decreases due to a decrease in the temperature of the pipette tip A depending on the internal temperature. In this case, as illustrated in FIG. 2B, the pipette tip A varies from the end height h1 to h1'. In a case where the reaction step is allowed to proceed as it is, the end of the pipette tip A becomes too high with respect to the reaction field, leading to the occurrence of residual liquid that is a prescribed amount or more in the reaction field in a case where the liquid is removed from the reaction field. Therefore, when the next liquid is supplied to the reaction field, the liquid newly supplied might be diluted by the residual liquid in the reaction field, hindering reaction with high accuracy. To cope with this, the height of the pipette nozzle B is corrected from the reference height h2 to h2' so as to cancel out the variation of the end height of the pipette tip A. That is, the height of the pipette nozzle B is corrected to make it lower with respect to the reaction field so as to set the end of the pipette tip A with respect to the reaction field to be at the predetermined height (h1).

The preferable timing of correcting the height of the pipette nozzle B from the reference height is one of immediately before supplying the liquid to the reaction field, and before the liquid is removed from the reaction field (immediately before removal, in particular) after the liquid has been supplied to the reaction field. Correcting the height of the pipette nozzle B from the reference height at such a timing enables the control of the positional relationship between the reaction field and the end of the pipette tip A with high accuracy. With the correction performed immediately before the supply of the liquid to the reaction field, it is possible to prevent the end of the pipette tip A from coming in contact with the reaction field or from bending due to the contact when the entire length of the pipette tip A increases. Moreover, with the correction of the height of the pipette nozzle B performed immediately before removal of the liquid from the reaction field, it is possible to control the amount of residual liquid in the reaction field with high accuracy.

It is preferable to correct the height of the pipette nozzle B in accordance with the elapsed time of the reaction step. The pipette tip A is influenced by the internal temperature around the pipette tip A during the reaction step. The end height of the pipette nozzle B gradually varies in accordance with the elapsed time of the reaction step. Therefore, with the correction of the height of the pipette nozzle B on the basis of the elapsed time of the reaction step, it is possible to easily and quickly cancel out the variation of the end of the pipette tip A without measuring the entire length of the pipette tip A. In addition, since the operation does not need any special equipment, and thus can be done at low cost and in a small space.

Moreover, the height of the pipette nozzle B is preferably corrected on the basis of a length on the pipette tip A between the end and a portion fitting with the pipette nozzle B, a linear expansion coefficient of the pipette tip A, a temperature variation of the pipette tip A with time, and the elapsed time of the reaction step. It is preferable that the height of the pipette nozzle B is corrected on the basis of the maximum change amount of the temperature of the pipette tip A in the reaction step, in addition to the above-described elements.

For example, the length on the pipette tip A from the end to the portion fitting with the pipette nozzle B is measured beforehand by an arbitrary measuring apparatus.

The linear expansion coefficient of the pipette tip A is determined for each of materials of the pipette tip A. The pipette tip A is preferably formed of resin from the viewpoint of being able to be easily and inexpensively manufactured. The linear expansion coefficient of the pipette tip A with the use of polypropylene is about $5.8 \times 10^{-5}/°$ C. to $12 \times 10^{-5}/°$ C., and the linear expansion coefficient of the pipette tip A with the use of polystyrene is about $6.0 \times 10^{-5}/°$ C. to $8.0 \times 10^{-5}/°$ C. In addition, the linear expansion coefficient of the pipette tip A with the use of polyethylene is about $11 \times 10^{-5}/°$ C. to $15 \times 10^{-5}/°$ C., and the coefficient of linear expansion of the pipette tip A with the use of low density polyethylene is about $16 \times 10^{-5}/°$ C. to $20 \times 10^{-5}/°$ C. Furthermore, the linear expansion coefficient of the pipette tip A with the use of fluororesin is about $10 \times 10^{-5}/°$ C. to $12 \times 10^{-5}/°$ C.

Figure 3:
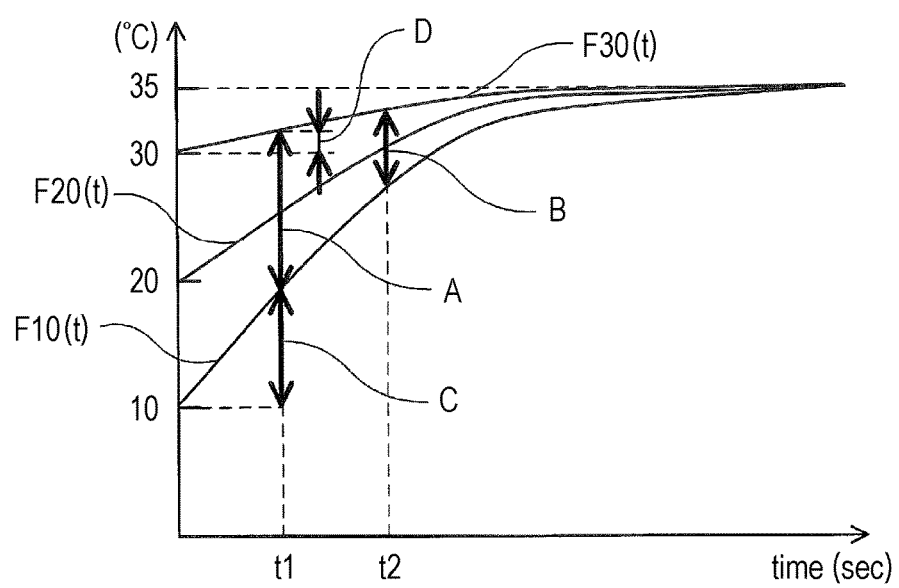
FIG. 3 is a graph illustrating a relationship between the temperature of the pipette tip and elapsed time of the reaction step.

Subsequently, the variation of the temperature of the pipette tip A with time will be described in detail with reference to FIG. 3. FIG. 3 is a graph illustrating a relationship between the temperature of the pipette tip A and the elapsed time of the reaction step after the first process. The horizontal axis of FIG. 3 is the elapsed time in the reaction step after the first process, and the vertical axis is the temperature (° C.) of the pipette tip A. In this illustration, the temperature of the pipette tip A when the pipette tip A is attached to the pipette nozzle B is in the range of 10 to 30 degrees. Furthermore, the internal temperature of the space in which the reaction step is performed was set to 37° C., and the maximum reachable temperature of the pipette tip A in the space was set to 35° C. Moreover, F10 in FIG. 3 is a function indicating a relationship between the elapsed time and the temperature of the pipette tip A in a case where the temperature of the pipette tip A when the pipette tip A is attached to the pipette nozzle B is 10° C. F20 is a function indicating a relationship between the elapsed time and the temperature of the pipette tip A in a case where the temperature of the pipette tip A when the pipette tip A is attached to the pipette nozzle B is 20° C. F30 is a function indicating a relationship between the elapsed time and the temperature of the pipette tip A in a case where the temperature of the pipette tip A when the pipette tip A is attached to the pipette nozzle B is 30° C.

As illustrated in FIG. 3, the relationship between the elapsed time of the reaction step and the temperature of the pipette tip A varies depending on the temperature of the pipette tip A when the pipette tip A is attached to the pipette nozzle B Thus, the relationship between the elapsed time of the reaction step and the temperature of the pipette tip A within the reaction space is to be obtained in advance. In a case where the temperature of the pipette tip A is not measured, it is difficult to determine a specific temperature, within the range of 10° C. to 30° C., of the pipette tip A in the first process. In this case, a temperature range that the temperature of the pipette tip A can take t1 second(s) after the start of the reaction step, after the end height of the pipette tip A is detected, corresponds to the range "A" illustrated in FIG. 3, while the temperature range that can be taken by the temperature of the pipette tip A after t2 seconds corresponds to the range "B" illustrated in FIG. 3.

Additionally, the maximum value of the change amount of the temperature of the pipette tip A after t1 second(s) is "C" illustrated in FIG. 3 and can be expressed by F10(t1)−F10(t0). Additionally, the minimum value of the change amount of the temperature of the pipette tip A after t1 second(s) is "D" illustrated in FIG. 3 and can be expressed by F30(t1)−F30(t0). As illustrated in FIG. 3, regarding the change amount of the temperature of the pipette tip A, the lower the temperature of the pipette tip A at the point of the first process (or immediately after the start of the reaction), the greater the temperature difference between the temperature and the maximum reachable temperature, leading to a greater change amount of the temperature of the pipette tip A after t seconds. In the example illustrated in FIG. 3, the maximum temperature change amount of the pipette tip A is 35° C.−10° C.=25° C.

The variation with time of the temperature of the pipette tip A (hereinafter also referred to as "temporal change function of the temperature of the pipette tip A") depends on the temperature (initial temperature), in the first process, of the pipette tip A and the internal temperature at which the reaction step is executed. The assumable case will be described below.

Case 1

In a case where the temperature (initial temperature), in the first process, of the pipette tip A is known, the temperature of the pipette tip A after t seconds can be estimated from the temporal change function of the temperature of the pipette tip A. Accordingly, it is possible to determine the height of the pipette nozzle B (correction amount) after the correction of the height of the pipette nozzle B from the reference height, with high accuracy.

Case 2

In a case where the temperature (initial temperature), in the first process, of the pipette tip A is unknown, temporal change functions F10 and F30 at the time when the temperatures (initial temperatures), in the first process, of the pipette tip A are the lowest 10° C. and the maximum 30° C., respectively, can be used to estimate the temperature of the pipette tip A after t seconds as being between F10(t) and F30(t), making it possible to perform approximate calculation of the height (correction amount) of the pipette nozzle B after the height of the pipette nozzle B has been corrected from the reference height.

Case 3

Furthermore, in a case where the variation of the temperature of the pipette tip A with time is unknown, the variation of the end of the pipette tip A due to the reaction time is unknown. Accordingly, the height of the pipette nozzle B is corrected from the reference height within a range of the maximum temperature change amount of the pipette tip A calculated from the temperature (initial temperature), in the first process, of the pipette tip A and the maximum reachable temperature of 35° C. In a case where correction is performed in consideration of this maximum temperature change amount, the reaction field and the end position of the pipette tip A would be separated from each other. Still, it is at least possible to prevent the end of the pipette tip A from colliding with the reaction field.

More specifically, it is possible to grasp a temperature difference corresponding to variation of the temperature of the pipette tip A from immediately after the first process in correction of the pipette nozzle B from the reference height on the basis of the variation in the temperature of the pipette tip A with time and the elapsed time of the reaction step described above. Subsequently, it is possible to grasp a change rate of the pipette tip A at the temperature difference corresponding to the variation on the basis of the temperature difference corresponding to the variation and the linear expansion coefficient of the pipette tip A. Subsequently, it is possible to estimate the variation amount of the end of the pipette tip A on the basis of the change rate and a length on the pipette tip A between the end and the portion fitting with the pipette nozzle B. Then, the correction amount of the pipette nozzle B is estimated on the basis of the variation. In this manner, the correction amount of the height of the pipette nozzle B is estimated on the basis of the length on the pipette tip A between the end and the portion fitting with the pipette nozzle B, the linear expansion coefficient of the pipette tip A, the temperature variation of the pipette tip A with time, and the elapsed time of the reaction step, making it possible to perform highly accurate positioning of the height of the pipette tip B after a predetermined time has elapsed in the reaction step without measuring the temperature of the pipette tip A.

Moreover, as illustrated in FIG. 3, it is preferable that the slope (change rate) of the temporal change function of the temperature of the pipette tip A decreases with elapsed time. When the internal temperature of the space in which the reaction step is performed is constant during the reaction step, the slope (change rate) of the temporal change function of the temperature of the pipette tip A decreases with elapsed time. The assumable case will be described below.

Case 1

The temperature of the pipette tip A may be estimated by measuring the internal temperature at the time of attaching the pipette tip A to the pipette nozzle B, using a first temperature measurement means. In this case, when the ambient temperature in the first process is known (for example, 20° C.), the temperature can be estimated to be substantially close to the initial temperature of the pipette tip A immediately after the application. Accordingly, F20 is selected as the temporal change function and the maximum change amount of the temperature of the pipette tip A after t1 second(s) can be expressed by F20 (t1)–F20 (t0). This amount is smaller than the maximum change amount (F10 (t1)–F10 (t0)) of the temperature of the pipette tip A after t1 second(s) in the case where the temperature of the pipette tip A in the first process is unknown, making it possible to correct the height of the nozzle B with high accuracy.

Case 2

In a case where the temperature (initial temperature), in the first process, of the pipette tip A is unknown, temporal change functions F10 and F30 at the time when the temperatures (initial temperature), in the first process, of the pipette tip A are the lowest 10° C. and the maximum 30° C., respectively, can be used to estimate the temperature of the pipette tip A after t seconds as being the temperature between F10(t) and F30(t), making it possible to perform approximate calculation of the height (correction amount) of the pipette nozzle B after the height of the pipette nozzle B has been corrected from the reference height. At this time, the maximum change amount of the temperature of the pipette tip A is F10 (t1)–F10 (t0) and the minimum change amount is F30 (t1)–F30 (t0). Accordingly, it is possible to calculate the correction amount with the temperature change amount of the pipette tip A being F30 (t1)–F30 (t0) or more and F10 (t1)–F10 (t0) or less and correct the height of the pipette nozzle B. From the viewpoint of avoiding the collision of the end of the pipette tip, it is more desirable to correct the height of the pipette nozzle B with the maximum correction amount calculated from the maximum change amount F10 (t1)–F10 (t0).

Case 3

In a case where the variation of the end of the pipette tip A due to the reaction time is unknown, the height of the pipette nozzle B is corrected from the reference height within a range of the maximum temperature change amount of the pipette tip A calculated from the temperature (initial temperature), in the first process, of the pipette tip A and the maximum reachable temperature of 35° C. In a case where the initial temperature is also unknown, the difference between the assumed minimum temperature (for example, 10° C.), in the first process, of the pipette tip A and the maximum reachable temperature of 35° C. would be the maximum temperature change amount. This maximum temperature change amount can be used to approximate the height (correction amount) of the pipette nozzle B after being corrected from the reference height, making it possible to perform correction of the height of the pipette nozzle B. In a case where correction is performed with this maximum temperature change amount, the reaction field and the end position of the pipette tip A would be separated from each other. Still, it is at least possible to prevent the end of the pipette tip A from colliding with the reaction field.

Effects

As described above, the reaction method according to the first embodiment sets the reference height of the pipette nozzle B on the basis of the end height of the pipette tip A and corrects the height of the pipette nozzle B from the reference height so as to cancel out the variation of the end height of the pipette tip A. Accordingly, it is possible to control the positional relationship (distance) between the reaction field and the end of the pipette tip A with high accuracy. This leads to highly accurate control of the reaction step, making it possible to obtain the result quantitatively with high sensitivity.

Second Embodiment

A reaction method according to a second embodiment is different from the reaction method according to the first embodiment in that the temperature of the pipette tip A is measured. The reaction method according to the second embodiment includes a first process of setting the reference height of the pipette nozzle B before the reaction step and a second process of correcting the height of the pipette nozzle B from the reference height in a course of the reaction step. The first process further performs measurement of the temperature of the pipette tip A by a second temperature measurement means. In the first process, the timing of measuring the temperature of the pipette tip A is preferably after the pipette tip A is attached to the pipette nozzle B and immediately before transition to the reaction step, more preferably about the same period as the first process.

The second process further performs measurement of the temperature of the pipette tip A by the second temperature measurement means, as well as corrects the height of the pipette nozzle B from the reference height in accordance with the difference between the temperature of the pipette tip A measured by the second temperature measurement means in the first process at the time when the end height of the pipette tip A was detected, and the temperature of the pipette tip A measured by the second temperature measurement means in the reaction step. In the second process, the temperature of the pipette tip A may be constantly measured.

In addition, the second process preferably corrects the height of the pipette nozzle B from the reference height on the basis of the length on the pipette tip A between the end and the portion fitting with the pipette nozzle B, the linear expansion coefficient of the pipette tip A, and a difference between the temperature (first temperature) of the pipette tip A when the end height of the pipette tip A is detected and the temperature of the pipette tip A (second temperature) in the reaction step. In this case, the temperature of the pipette tip A is measured to enable precisely grasping the height variation of the pipette tip A, leading to achievement of control of the pipette nozzle B with high accuracy.

More specifically, the pipette tip A is formed of polypropylene, and the linear expansion coefficient of the pipette tip A is $10 \times 10^{-5}/°$ C. Moreover, the length on the pipette tip A from the end to the portion fitting with the pipette nozzle B is set to 70 mm. Moreover, the temperature when the pipette tip A is attached to the pipette nozzle B and the end height of the pipette tip A is detected is set to 10° C. Then, in the reaction space, the temperature of the pipette tip A is assumed to increase up to 35° C. That is, it is assumed that the temperature of the pipette tip B has changed from 10° C. to 35° C. In this case, the pipette tip A expands by 175 μm. For example, in operation of removing a liquid from the reaction field, there is a case where it is desired to control the distance between the reaction field and the end of the pipette tip A to 100 μm or less in order to reduce the amount of liquid in the reaction field. In a case where it is desired to control the distance between the reaction field and the end of the pipette tip A with high accuracy, the end of the pipette tip A would come into contact with the reaction field. Accordingly, the reference height of the pipette nozzle B is corrected by the extent of expansion of the pipette tip A. In this case, the height is moved by 175 μm upwardly.

Effects

As described above, the temperature of the pipette tip A is measured in the reaction method according to second embodiment. Accordingly, the height of the pipette nozzle A can be corrected from the reference height with higher accuracy compared with the reaction method according to the first embodiment. With this configuration, it is possible to control the positional relationship (distance) between the reaction field and the end of the pipette tip A with higher accuracy. Moreover, this makes it possible to control the reaction step with high accuracy, and to obtain the result quantitatively with high sensitivity.

In the first embodiment and the second embodiment, the temperature of the pipette tip A may be controlled by a temperature adjustment mechanism. In this case, it is possible not only to maintain the temperature of the pipette tip A as a constant level but also to maintain the temperature of the liquid after suction, leading to achievement of reaction with higher accuracy. In particular, this would be further effective for maintaining the temperature inside the pipette tip in a case where suction and discharge by a pump are repeated a plurality of times and the reaction solution is delivered back and forth a plurality of times within the reaction field and the pipette tip. Additionally, when the reaction field and a liquid reservoir are separated, or in a case where the temperature of the liquid reservoir is not adjusted in the reaction space, it is possible to perform preliminary temperature control within the pipette, which is effective.

The second embodiment is a case where the temperature of the pipette tip A is measured twice, that is, in the first process and the second process, by the second temperature measurement means, and the correction amount is calculated from the temperature difference. Alternatively, however, it is allowable to perform the measurement of the temperature of the pipette tip A solely in the first process, and use the temperature (initial temperature) (for example, 30° C.) of the pipette tip A obtained in first process and use F30 as the temporal change function at that temperature, making it possible to express the maximum change amount in the temperature of the pipette tip A after t1 second(s) by $F30(t1) - F30(t0)$. This amount is smaller than the maximum change amount ($F10(t1) - F10(t0)$) of the temperature of the pipette tip A after t1 second(s) in the case where the temperature of the pipette tip A in the first process is unknown, making it possible to correct the height of the nozzle B with high accuracy. This decreases the correction accuracy compared with the case where the temperature of the pipette tip A is also measured in the second process of the second embodiment. Still, it is an effective means when precise measurement of the temperature of the pipette tip A is difficult in the second process for some reasons. It is effective, for example, in a case where an error occurs in the temperature measurement of the pipette tip A due to the influence of the temperature adjustment (heater) of the pipette tip A arranged nearby. In addition, it would be useful in a case where the temperature of the pipette tip A is measured while the temperature adjustment of the pipette tip A is turned off in the first process and, then, the temperature adjustment of the pipette tip A is turned on to allow reaction at a stable temperature in the subsequent reaction step.

SPFS Apparatus

Next, as an example of an apparatus for performing the reaction method according to the above-described first and second embodiments, a surface plasmon-field enhanced fluorescence analyzer (SPFS apparatus) to detect the presence or amount of a detection target substance contained in the specimen will be described.

First Configuration of SPFS Apparatus

Figure 4:
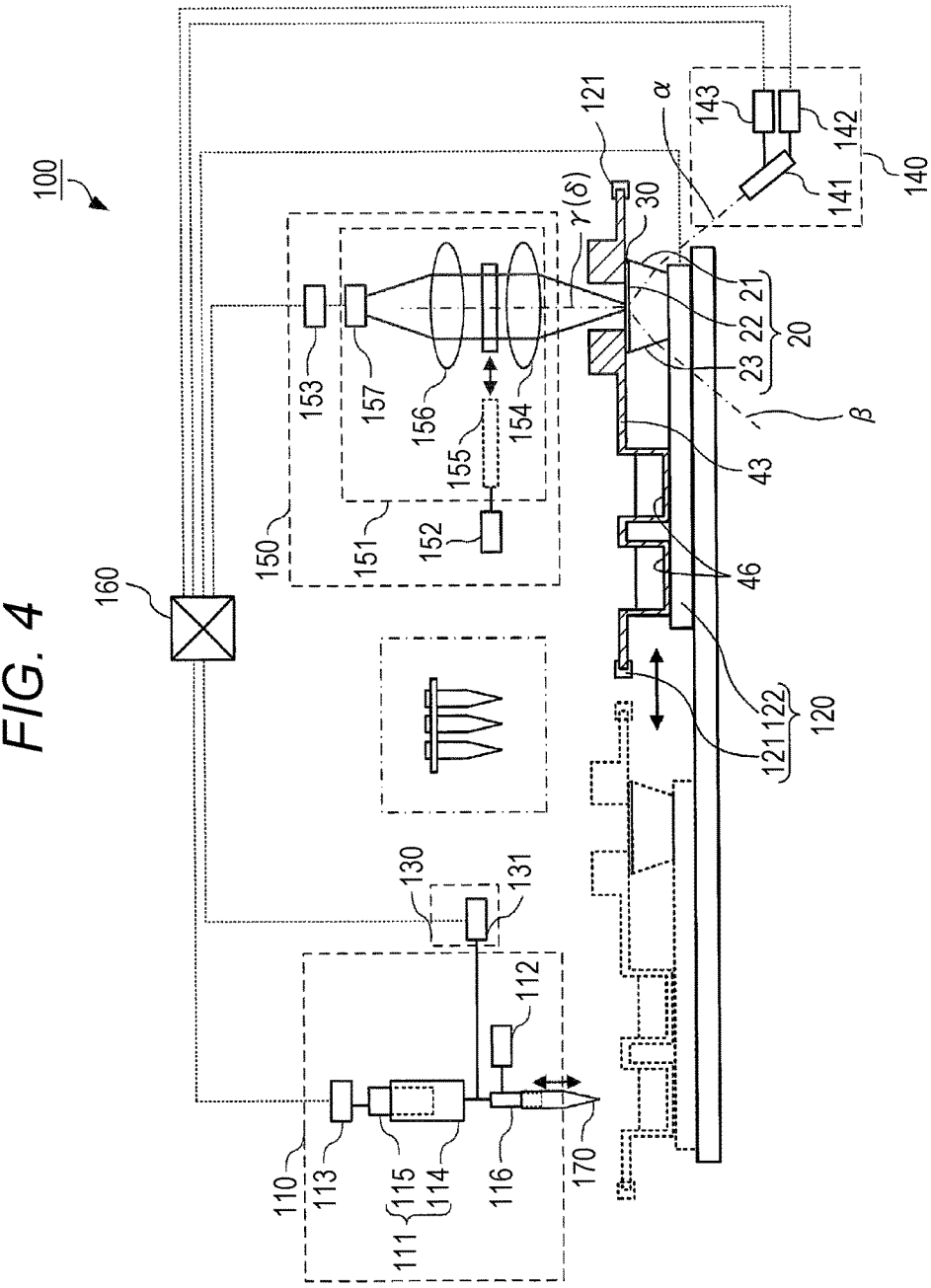
FIG. 4 is a schematic diagram illustrating a configuration of an SPFS apparatus.

FIG. 4 is a schematic diagram illustrating a configuration of a surface plasmon-field enhanced fluorescence analyzer (SPFS apparatus) 100 capable of performing the reaction method according to the first embodiment.

As illustrated in FIG. 4, the SPFS apparatus 100 includes a liquid delivery unit 110 including a pipette 111 and a pipette moving unit 112, a conveyance unit 120 including a chip holder 121, a position information acquisition unit 130, a light emitting unit 140, a photodetector 150, and a control unit 160. The SPFS apparatus 100 is used with the detection chip 10 attached to the chip holder 121. Accordingly, the detection chip 10 will be described first, and individual constituent members of the SPFS apparatus 100 will be described thereafter.

Configuration of Detection Chip

Figure 5A:
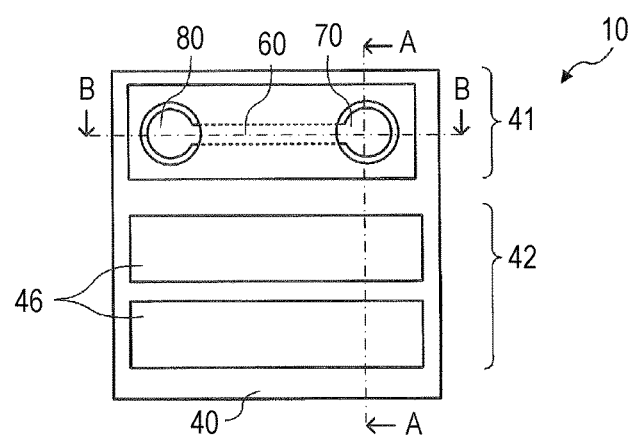
FIGS. 5A to 5C are diagrams illustrating a configuration of a detection chip.
Figure 5B:
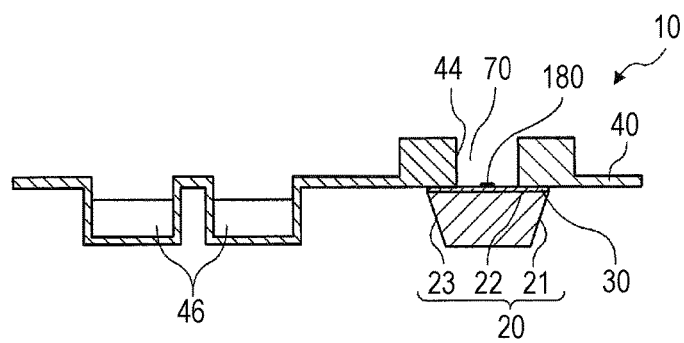
Figure 5C:
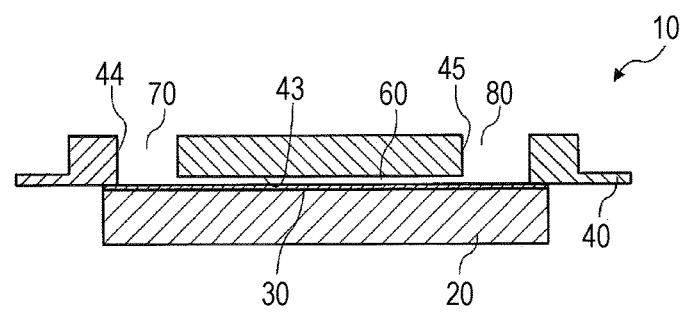
Figure 6:
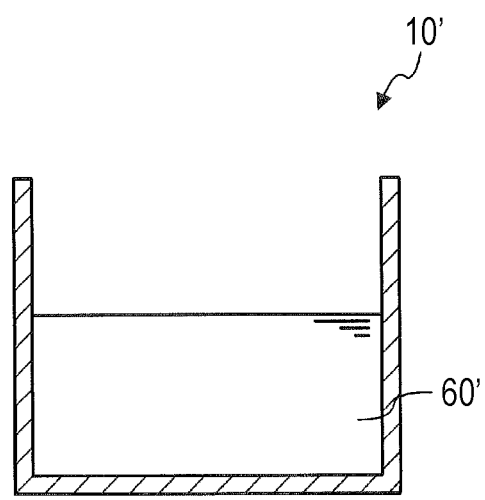
FIG. 6 is a schematic cross-sectional view of a detection chip according to another embodiment.

FIG. 5 is a diagram illustrating a configuration of the detection chip 10. FIG. 5A is a plan view of the detection chip 10. FIG. 5B is a cross-sectional view taken along line A-A illustrated in FIG. 5A. FIG. 5C is a cross-sectional view taken along line B-B illustrated in FIG. 5A. FIG. 6 is a schematic cross-sectional view illustrating another embodiment of the detection chip 10.

As illustrated in FIGS. 5A to 5C, the detection chip 10 includes: a prism 20 having an incident surface 21, a film forming surface 22 and an emission surface 23; a metal film 30; and a flow path lid 40 including a reaction region 41 and a reagent storage region 42. The metal film 30 and the flow path lid 40 are arranged on the film forming surface 22 of the prism 20. The flow path 60 that allows a liquid to flow is formed by the prism 20, the metal film 30 and the flow path lid 40. The flow path 60 is arranged directly on the film forming surface 22 of the prism 20 or via the metal film 30. The detection chip 10 may be either a reusable chip or a disposable chip. In the present embodiment, the detection chip 10 is a disposable chip. Examples of the liquid flowing through the flow path 60 include a specimen containing a detection target substance (for example, blood, serum, plasma, urine, nostrils, saliva, and semen), a labeling liquid including a capture agent labeled with a fluorescent substance, and a washing liquid.

The prism 20 is formed of an insulator transparent to excitation light $\alpha$. The incident surface 21 of the prism 20 causes the excitation light $\alpha$ from the light emitting unit 140 to be incident onto the inside of the prism 20. The metal film 30 is arranged on the film forming surface 22. In the present embodiment, the excitation light $\alpha$ incident on the inside of the prism 20 is applied onto the metal film 30 on which the detection target substance is captured. The excitation light $\alpha$ is reflected on the back surface of the metal film 30 to be reflected light $\beta$. More specifically, the excitation light $\alpha$ is reflected by an interface (film forming surface 22) between the prism 20 and the metal film 30 to be the reflected light $\beta$. The emission surface 23 causes the reflected light to be emitted to the outside of the prism 20.

The shape of the prism 20 is not particularly limited. In the present embodiment, the shape of the prism 20 is a columnar body having a trapezoidal bottom surface. The surface corresponding to one bottom side of the trapezoid is the film forming surface 22, the surface corresponding to one leg is the incident surface 21, and the surface corresponding to the other leg is the emission surface 23. The trapezoid as the bottom surface is preferably an isosceles trapezoid. With this shape, the incident surface 21 and the emission surface 23 are symmetrical to each other, capable of suppressing the stay of an S wave component of the excitation light $\alpha$ within the prism 20.

The incident surface 21 is formed to suppress the return of the excitation light $\alpha$ to the light emitting unit 140. In the case where the light source of the excitation light $\alpha$ is a laser diode (hereinafter also referred to as "LD"), the return of the excitation light $\alpha$ to the LD would disturb an excited state of the LD, causing variation of the wavelength and output of the excitation light $\alpha$. Therefore, in the scanning range including the enhancement angle at a center, the angle of the incident surface 21 is set so as to avoid perpendicular incidence of the excitation light $\alpha$ to the incident surface 21. Note that the "enhancement angle" refers to an incident angle that maximizes the light amount of scattered light (hereinafter referred to as "plasmon scattered light") $\gamma$ having a wavelength same as the excitation light $\alpha$ emitted above the detection chip 10 when scanning of the incident angle of the excitation light a with respect to the metal film 30 is performed. In the present embodiment, the angle between the incident surface 21 and the film forming surface 22 and the angle formed between the film forming surface 22 and the emission surface 23 are both about 80°.

Note that the enhancement angle is substantially determined by the design of the detection chip 10. The design elements are a refractive index of the prism 20, a refractive index of the metal film 30, a film thickness of the metal film 30, the extinction coefficient of the metal film 30, the wavelength of the excitation light $\alpha$, or the like. While the enhancement angle is shifted by the detection target substance captured on the metal film 30, the shifted amount is below several degrees.

Meanwhile, the prism 20 has considerable degree of a birefringence characteristic. Examples of the material of the prism 20 include an insulating resin and glass. The material of the prism 20 is preferably a resin having a refractive index of 1.4 to 1.6 and a small birefringence.

The metal film 30 is arranged so as to be exposed to at least a portion of the flow path 60 on the film forming surface 22 of the prism 20. The metal film 30 enables generation of interaction (SPR) between the photons of the excitation light $\alpha$ incident on the film forming surface 22 under the total reflection condition and the free electrons inside the metal film 30. The metal film 30 also enables generation of localized field light (generally referred to as "evanescent light" or "near-field light") on the surface of the metal film 30.

The material of the metal film 30 is not particularly limited as long as it is a metal capable of generating SPR. Examples of the material of the metal film 30 include gold, silver, copper, aluminum, and alloys of these metals. In the present embodiment, the metal film 30 is a gold thin film. The method of forming the metal film 30 is not particularly limited. Examples of the method of forming the metal film 30 include sputtering, vapor deposition, and plating. The thickness of the metal film 30 is not particularly limited, but it is preferably within the range of 30 to 70 nm.

Moreover, although not specifically illustrated, a capture agent for capturing the detection target substance is fixed on the surface of the metal film 30. The fixed capture agent on the metal film 30 makes it possible to selectively detect the detection target substance. In the present embodiment, the capture agent is uniformly immobilized in a predetermined region on the metal film 30. The region where the capture agent is immobilized corresponds to a reaction field where primary and secondary reactions described below occur. The capture agent immobilized to the metal film 30 is exposed in the flow path 60. The type of the capture agent is not particularly limited as long as it can capture the detection target substance. In the present embodiment, the capture agent is a whole of or a fragment of an antibody capable of specifically binding to the detection target substance.

The flow path lid 40 is arranged above the film forming surface 22. As described above, the flow path lid 40 has the reaction region 41 and the reagent storage region 42. The reaction region 41 is a region in which a primary reaction and a secondary reaction described below are performed. The reagent storage region 42 is a region to store the labeling liquid used for the secondary reaction, the washing liquid used for washing after individual reactions, or the like. A flow path groove 43 to be the flow path 60 is formed on the back surface of the reaction region 41 in the flow path lid 40. In addition, a first through hole 44 serving as an injection portion 70 and a second through hole 45 serving as a reservoir 80 open in a front surface and a back surface, respectively, of the reaction region 41. Each of ends of the flow path groove 43 is connected to the first through hole 44 and the second through hole 45, respectively. The reagent storage region 42 includes a recess 46 opening on the front surface. The number of the recesses 46 is not particularly limited. In the present embodiment, the number of the recesses 46 is two. The recess 46 stores a labeling liquid used for the secondary reaction, a washing liquid, or the like. The flow path groove 43, the first through hole 44, and the second through hole 45 form the flow path 60, the injection portion 70, and the reservoir 80 by stacking the prism 20, the metal film 30, and the flow path lid 40 in this order.

The flow path lid 40 is preferably formed of a material transparent to a fluorescence δ and plasmon scattered light γ emitted from the metal film 30. Examples of the material of the flow path lid 40 include resins. The flow path lid 40 may be formed of an opaque material at the other part as long as the portion for extracting the fluorescence δ and the plasmon scattered light γ to the outside is transparent to the fluorescence δ and the plasmon scattered light γ. The flow path lid 40 is joined to the prism 20 or the metal film 30 by bonding with a double-faced tape or an adhesive, laser welding, ultrasonic welding, crimping using a clamp member, or the like.

As illustrated in FIG. 6, a detection chip 10' may have a well 60' instead of the flow path 60. The detection chip 10' is used by injecting or removing a liquid at an opening of the well 60'. At this time, the reaction field may be formed in such a manner that the capture agent is immobilized to the bottom of the well or the wall surface of the well beforehand and react with the detection target substance in a solution, or alternatively, that such a capture agent is not immobilized and liquid-liquid reaction occurs in a solution in the well.

As illustrated in FIG. 4, the excitation light α is incident on the incident surface 21 into the prism 20. The excitation light α incident into the prism 20 is applied to the metal film 30 at a total reflection angle (angle at which SPR occurs). Application of the excitation light α to the metal film 30 at an angle at which SPR occurs enables localized field light to be generated on the metal film 30. This localized field light excites a fluorescent substance to label the detection target substance present on the metal film 30 so as to release the fluorescence δ. The SPFS apparatus 100 measures the light amount of the fluorescence δ released from the fluorescent substance to detect the presence or amount of the detection target substance.

Configuration of SPFS Apparatus

Next, constituent members of the SPFS apparatus 100 according to the present embodiment will be described. As described above, the SPFS apparatus 100 includes the liquid delivery unit 110, the conveyance unit 120, the position information acquisition unit 130, the light emitting unit 140, the photodetector 150, and the control unit 160. The detection chip 10 can be held by the chip holder 121 of the conveyance unit 120.

The liquid delivery unit 110 includes a liquid delivery pump 111, a pipette nozzle 116, a pipette nozzle drive mechanism 112, and a liquid delivery pump drive mechanism 113. The liquid delivery unit 110 injects a specimen into the flow path 60 of the detection chip 10 held in the chip holder 121 or moves a liquid, such as a labeling liquid or a washing liquid stored in the reagent storage region 42 of the detection chip 10, to the inside of the flow path 60 of the reaction region 41. The liquid delivery unit 110 also discharges the liquid from the flow path 60 or stirs the liquid within the flow path 60. The liquid delivery unit 110 is used in a state where a pipette tip 170 is attached to the pipette nozzle 116. From the viewpoint of preventing contamination with impurities or the like, it is preferable that the pipette tip 170 be exchangeable.

The liquid delivery pump 111 sucks a liquid when supplying the liquid to the flow path 60 or removing the liquid from the flow path 60. The liquid delivery pump 111 includes a syringe 114, a plunger 115 capable of reciprocating in the syringe 114, and, a pipette nozzle 116 being connected to the syringe 114. Moreover, the liquid delivery pump 111 can quantitatively suck and discharge the liquid by the reciprocating motion of the plunger 115. This enables the liquid delivery pump 111 to supply a liquid to the flow path 60 or remove the liquid from the flow path 60. Moreover, the liquid delivery pump 111 can stir the liquid in the flow path 60 by repeating suction and discharge of the liquid.

The pipette nozzle drive mechanism 112 moves the pipette nozzle 116 in order to supply the liquid into the flow path 60 via the injection portion 70 and to remove the liquid from the flow path 60 via the injection portion 70. In addition, the pipette nozzle drive mechanism 112 moves the above-described pipette nozzle 116 in order to correct the height of the pipette nozzle 116 from the reference height. For example, the pipette nozzle drive mechanism 112 freely moves the pipette nozzle 116 in an axial direction (for example, in the vertical direction) of the pipette nozzle 116. The pipette nozzle drive mechanism 112 includes a solenoid actuator and a stepping motor, for example.

The liquid delivery pump drive mechanism 113 moves the plunger 115 to aspirate the external liquid into the pipette tip 170 and to discharge the liquid in the pipette tip 170 to the outside. The liquid delivery pump drive mechanism 113 includes an apparatus for reciprocating the plunger 115, such as a stepping motor. From the viewpoint of managing a residual liquid amount of the detection chip 10, it is preferable to use the stepping motor because of its capability of managing the liquid delivery amount and the liquid delivery speed of the liquid delivery pump 111.

As described above, the liquid delivery unit 110 sucks various liquids from the recess 46 and supplies the liquids to the flow path 60 of the detection chip 10. At this time, the reciprocating motion of the plunger 115 in the flow path 60 with respect to the syringe 114 is repeated in a state in which the end of the pipette tip 170 is close to the bottom surface of the flow path 60. Thereby, the liquids inside the inside of the flow path 60 in the detection chip 10 are allowed to reciprocate and the liquid in the flow path 60 is stirred. This makes it possible to achieve a uniform concentration of the liquid and promotion of reactions (for example, the primary reaction and the secondary reaction) in the flow path 60.

The liquid in the flow path 60 is sucked again by the liquid delivery pump 111 and discharged to a waste liquid tank, which is not illustrated, or the like. Repetition of the operation enables implementation of reactions, washing, or the like with various liquids and arrangement of the detection target substance labeled with a fluorescent substance in a reaction field in the flow path 60. Note that when the liquid is removed from the inside of the flow path 60, the height of the pipette nozzle 116 is corrected from the reference height so as to cancel out the variation in the end height of the pipette tip 170, as described above.

The conveyance unit 120 conveys the detection chip 10 to an attachment position, a detection position, or a liquid delivery position, while holding the detection chip 10. Note that the "attachment position" is a position where the pipette tip 170 is attached to the pipette nozzle 116. The "detection position" is a position at which the light emitting unit 140 applies the excitation light α to the detection chip 10 and at which the photodetector 150 detects the fluorescence δ or the plasmon scattered light γ generated in consequence of the application. Moreover, the "liquid delivery position" is a position at which the liquid delivery unit 110 injects a liquid into the flow path 60 of the detection chip 10 or removes the liquid from inside of the flow path 60 of the detection chip 10. The conveyance unit 120 includes a chip holder 121 and a conveyance stage 122. The "attachment position" and the "detection position" may be the same position.

The chip holder 121 is fixed to the conveyance stage 122, and detachably holds the detection chip 10. The shape of the chip holder 121 is not particularly limited as long as it can hold the detection chip 10 and would not disturb optical paths of the excitation light α, the fluorescence δ and the plasmon scattered light γ. In the present embodiment, the chip holder 121 has a shape capable of holding the detection chip 10 with the flow path lid 40 interposed therebetween.

The conveyance stage 122 moves the chip holder 121 in one direction and in the other direction opposite thereto (left and right direction on the paper surface of FIG. 1). The conveyance stage 122 is also shaped so as not to obstruct the optical paths of the excitation light α, the fluorescence δ and the plasmon scattered light γ. The conveyance stage 122 is driven by a stepping motor, for example.

The position information acquisition unit 130 obtains the end height of the pipette tip 170. The position information acquisition unit 130 is not particularly limited as long as it can obtain information related to the end height of the pipette tip 170. In the present embodiment, the position information acquisition unit 130 includes an air pressure sensor 131. The air pressure sensor 131 is connected between the pipette nozzle 116 and the syringe 114. The type of the air pressure sensor 131 is not particularly limited as long as it can measure the air pressure (pressure) inside the pipette tip 170. Examples of types of the air pressure sensor 131 include a mechanical sensor using a Bourdon tube and an electronic sensor using a semiconductor or the like.

In the present embodiment, the end height of the pipette tip 170 is obtained by measurement of the change in the air pressure within the pipette tip 170 by the air pressure sensor 131 when a gas is sucked or discharged at the end of the pipette tip 170 while changing the interval between the pipette tip 170 and the reference portion 180. The reference portion 180 may be a solid or a liquid, and is not particularly limited as long as its height is specified with high accuracy. Examples of the solid reference portion 180 include the flow path lid 40, a seal 50, the prism 20 (bottom surface of the flow path 60) in the detection chip 10. Other examples of the reference portion 180 in the SPFS apparatus 100 include the conveyance stage 122, the chip holder 121, and an arrangement surface (portion located below the pipette nozzle 116) on which the conveyance stage 122 is arranged in the conveyance unit 120. Examples of the liquid reference portion 180 include a liquid surface of the liquid stored in the recess 46 of the detection chip 10, a liquid surface of the liquid in the flow path 60, or the like. In order to manage the reaction field and the end position of the pipette tip 170 with high accuracy, it is desirable to more directly use the position of the reaction field as the reference portion 180, and it is more desirable to set the prism 20 (bottom surface of the flow path 60) as the reference portion 180.

In the operation of detecting the end height of the pipette tip 170, suction or discharge of a gas at the end of the pipette tip 170 may be performed continuously or intermittently. For example, in the case of discharging the gas, the output of the air pressure sensor 131 is detected while changing the distance between the end position of the pipette tip 170 and the reference portion 180 while discharging the gas from the end of the pipette tip 170 using the liquid delivery pump 111. When the output value is equal to or more than a threshold, it is determined that the end of the pipette tip 170 is in the vicinity of the reference portion 180, and the end position of the pipette tip 170 is detected. It is preferable to appropriately adjust the threshold used in the determination in accordance with the reference portion 180. In a case where the reference portion 180 is solid, the threshold can be set to be a higher pressure level than the case where the reference portion 180 is liquid. The sensor for detecting the end height of the pipette tip 170 in the first process may be other various sensors, such as a contact-type pressure sensor, a load cell, or a non-contact image sensor, other than the air pressure sensor as long as it can detect the end height with high accuracy. Since the liquid is not yet sucked to the pipette tip 170 in the first process, there is no need to worry about contamination of the apparatus, and thus, a contact type sensor as well as a non-contact type can be used.

The light emitting unit 140 applies the excitation light α toward the incident surface 21 of the detection chip 10 held by the chip holder 121. In the measurement of fluorescence δ or plasmon scattered light δ, the light emitting unit 140 emits P waves alone to the metal film 30 toward the incident surface 21 so as to allow the incident angle on the metal film 30 to be an angle capable of generating SPR. Note that the "excitation light" is light which directly or indirectly excites a fluorescent substance. For example, the excitation light α is light that generates localized field light that excites the fluorescent substance on the surface of the metal film 30 when the light is applied to the metal film 30 via the prism 20 at an angle capable of generating SPR. The light emitting unit 140 includes a light source unit 141, an angle adjustment mechanism 142, and a light source control unit 143.

The light source unit 141 emits the collimated excitation light α having a constant wavelength and light amount so as to obtain a substantially circular shaped irradiation spot on the back surface of the metal film 30. The light source unit 141 includes, for example, a light source of the excitation light α, a beam shaping optical system, an APC mechanism, and a temperature adjustment mechanism (none of them are illustrated).

The type of the light source is not particularly limited, and an example of this is a laser diode (LD). Other examples of light sources include light emitting diodes, mercury lamps, and other laser light sources. In a case where the light emitted from the light source is not a beam, the light emitted from the light source is converted into a beam by a lens, a mirror, a slit or the like. In a case where the light emitted from the light source is not monochromatic light, the light emitted from the light source is converted into monochromatic light by a diffraction grating or the like. Furthermore, when the light emitted from the light source is not linearly polarized light, the light emitted from the light source is converted into linearly polarized light by a polarizer or the like.

The beam shaping optical system includes, for example, a collimator, a band pass filter, a linear polarization filter, a half wave plate, a slit, a zooming means, or the like. The beam shaping optical system may include all or a portion of them. The collimator collimates the excitation light α emitted from the light source. The band pass filter filters the excitation light α emitted from the light source to obtain narrow band light having a center wavelength alone. This is because the excitation light α from the light source has a slight wavelength distribution width. The linear polarization filter filters the excitation light α emitted from the light source to obtain completely linearly polarized light. The half wave plate adjusts the polarization direction of the excitation light α so as to allow the P wave component to be incident on the metal film 30. The slit and the zooming means adjust the beam diameter and the outline shape of the excitation light α to obtain a circular shaped irradiation spot of a predetermined size on the back surface of the metal film 30. The APC mechanism controls the light source so as to obtain a constant output of the light source. More specifically, the APC mechanism detects the light amount of light branched from the excitation light α using a photodiode, which is not illustrated, or the like. Then, the APC mechanism controls the input energy by a regression circuit to control the output of the light source to be constant.

The angle adjustment mechanism 142 adjusts the incident angle of the excitation light α to the metal film 30 (interface between the prism 20 and the metal film 30 (film forming surface 22)). In order to apply the excitation light α at a predetermined incident angle toward a predetermined position of the metal film 30 via the prism 20, the angle adjustment mechanism 142 moves the optical axis of the excitation light α and the chip holder 121 relative to each other.

For example, the angle adjustment mechanism 142 pivots the light source unit 141 about an axis orthogonal to the optical axis of the excitation light α (an axis perpendicular to the paper surface of FIG. 4). At this time, the position of the rotation axis is set so as to substantially fix the position of the irradiation spot on the metal film 30 even when the incident angle is scanned. By setting the position of the rotation center to the vicinity of an intersection of the optical axes of the two beams of excitation light α at both ends of the scanning range of the incident angle (between the irradiation position on the film forming surface 22 and the incident surface 21), the shift of the irradiation position can be minimized.

As described above, the angle maximizing the light amount of the plasmon scattered light γ among the incident angles of the excitation light α to the metal film 30 is the enhancement angle. By setting the incident angle of the excitation light α at or in the vicinity of the enhancement angle, it is possible to measure the fluorescence δ with high intensity. While basic incident conditions of the excitation light α are determined by the material and shape of the prism 20 of the detection chip 10, the film thickness of the metal film 30, the refractive index of the liquid in the flow path 60, or the like, the optimum incident condition varies slightly depending on the type and the amount of the fluorescent substance in the flow path 60, the shape error of the prism 20, or the like. For this reason, it is preferable to determine the optimum enhancement angle for each of the measurements.

The light source control unit 143 controls various devices included in the light source unit 141 so as to control emission of the excitation light α from the light source unit 141. The light source control unit 143 includes a known computer or a microcomputer including an arithmetic apparatus, a control apparatus, a storage apparatus, an input apparatus, and an output apparatus.

When the light emitting unit 140 applies the excitation light α to the metal film 30 of the detection chip 10, the photodetector 150 detects the light amount of the fluorescence δ emitted from the vicinity of the surface of the metal film 30 on the flow path 60 side. If necessary, the photodetector 150 also detects plasmon scattered light γ generated by the emission of the excitation light α to the metal film 30. The photodetector 150 includes a light receiving unit 151, a position switching mechanism 152, and a sensor control unit 153.

The light receiving unit 151 is arranged in a direction normal to the surface of the metal film 30 of the detection chip 10. The light receiving unit 151 includes a first lens 154, an optical filter 155, a second lens 156, and a light receiving sensor 157.

The first lens 154 is a condenser lens, for example, and condenses light emitted from the metal film 30. The second lens 156 is an imaging lens, for example, and focuses the light condensed by the first lens 154 onto a light receiving surface of the light receiving sensor 157. The optical path between the first lens 154 and the second lens 156 is substantially parallel.

The optical filter 155 is arranged between the first lens 154 and the second lens 156. The optical filter 155 selectively guides the fluorescent component to the light receiving sensor 157, and removes the excitation light component (plasmon scattered light γ) in order to detect the fluorescence δ with a high S/N ratio. Examples of the optical filter 155 include an excitation light reflection filter, a short wavelength cut-off filter, and a band pass filter. The optical filter 155 is, for example, a filter including a multilayer film that reflects a predetermined light component, or a color glass filter that absorbs a predetermined light component.

The light receiving sensor 157 detects the fluorescence δ and the plasmon scattered light γ. The light receiving sensor 157 has a high sensitivity capable of detecting weak fluorescence δ from a trace amount of the detection target substance. Examples of the light receiving sensor 157 include a photomultiplier tube (PMT), an avalanche photodiode (APD), and a silicon photodiode (SiPD).

The position switching mechanism 152 switches the position of the optical filter 155 to position on the optical path or position outside the optical path in the light receiving unit 151. Specifically, when the light receiving sensor 157 detects the fluorescence δ, the optical filter 155 is arranged on the optical path of the light receiving unit 151, and when the light receiving sensor 157 detects the plasmon scattered light γ, the optical filter 155 is arranged at the outside of optical path of the light receiving unit 151.

The sensor control unit 153 controls detection of an output value of the light receiving sensor 157, the management of the sensitivity of the light receiving sensor 157 by the detected output value, the change of the sensitivity of the light receiving sensor 157 for obtaining an appropriate output value, or the like. The sensor control unit 153 includes a well-known computer or a microcomputer including an arithmetic apparatus, a control apparatus, a storage apparatus, an input apparatus, and an output apparatus.

The control unit 160 controls the liquid delivery pump drive mechanism 113, the conveyance stage 122, the angle adjustment mechanism 142, the light source control unit 143, the position switching mechanism 152, and the sensor control unit 153. The control unit 160 includes a well-known computer or a microcomputer including an arithmetic apparatus, a control apparatus, a storage apparatus, an input apparatus, and an output apparatus. The length on the above-described pipette tip 170 between the end and the portion fitting with the pipette nozzle 116, the linear expansion coefficient of the pipette tip 170, the maximum change amount of the temperature of the pipette tip 170 in the reaction step, and the variation with time in the temperature of the pipette tip 170 are stored beforehand in the storage apparatus. Moreover, the control unit 160 sets the reference height of the pipette nozzle 116 on the basis of the end height of the pipette tip 170 in the first process. Moreover, the control unit 160 obtains a correction amount for correcting the height of the pipette nozzle 116 from the reference height in the second process.

Detection Operation of SPFS Apparatus

Figure 7:
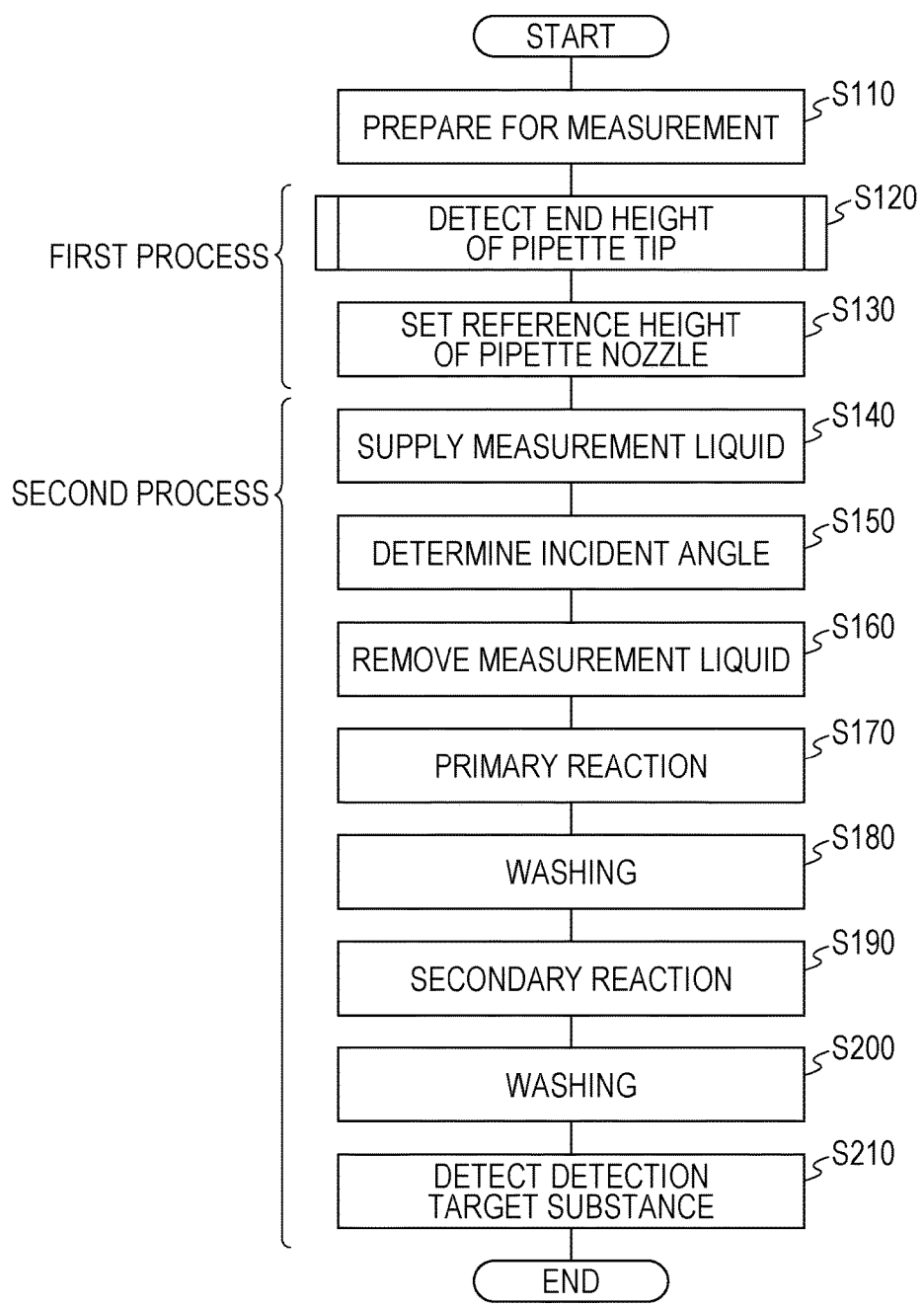
FIG. 7 is a flowchart illustrating operation of the SPFS apparatus according to the first embodiment.
Figure 8:
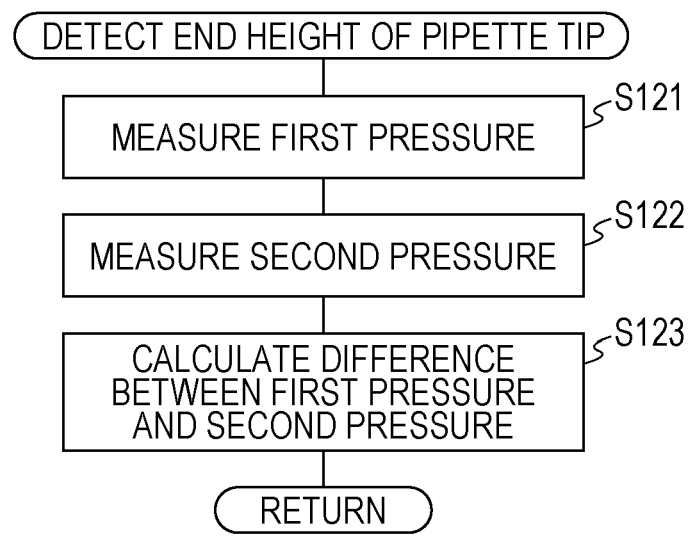
FIG. 8 is a flowchart illustrating details of a step of detecting an end height of a pipette tip.

Next, operation of detecting a detection target substance by the SPFS apparatus 100 will be described. FIG. 7 is a flowchart illustrating an exemplary operation procedure of the SPFS apparatus 100. FIG. 8 is a flowchart illustrating details of the step (step S120 in FIG. 7) of detecting the end height of the pipette tip 170. In this example, the primary antibody is immobilized on the metal film 30 as a capture agent. As a capture agent used for fluorescent labeling, a secondary antibody labeled with a fluorescent substance is used. Moreover, the bottom surface (metal film 30) of the flow path 60 is defined as the reference portion 180.

A first step is preparation for measurement (step S110). Specifically, the detection chip 10 is prepared, and the detection chip 10 is set on the chip holder 121 at a setting position of the detection chip 10. Moreover, at the attachment position, the pipette tip 170 is attached to the end portion of the pipette nozzle 116.

Next, the end height of the pipette tip 170 is detected (step S120). First, a first pressure in the pipette tip 170 is measured (step S121). Specifically, the control unit 160 drives the pipette nozzle drive mechanism 112 to move the end of the pipette tip 170 to a position directly above the bottom surface (reference portion) of the flow path 60. Then, the control unit 160 drives the liquid delivery pump drive mechanism 113 to allow the plunger 115 to proceed with respect to the syringe 114, and measures the first pressure in the pipette tip 170 by the air pressure sensor 131 while continuously ejecting air from the end of the pipette tip 170.

Next, the second pressure inside the pipette tip 170 is measured (step S122). Specifically, the control unit 160 drives the pipette nozzle drive mechanism 112 to move the end of the pipette tip 170 closer to the bottom surface (reference portion 180) side of the flow path 60 than in the step (step S121) of measuring the first pressure. Then, the control unit 160 drives the liquid delivery pump drive mechanism 113 to allow the plunger 115 to proceed with respect to the syringe 114, and measures the second pressure in the pipette tip 170 by the air pressure sensor 131 while continuously ejecting air from the end of the pipette tip 170.

Next, a difference between the first pressure and the second pressure is obtained (step S123). Specifically, the control unit 160 obtains the difference between the first pressure and the second pressure by subtracting the second pressure (the first pressure) from the first pressure (the second pressure). At this time, the pipette nozzle drive mechanism 112 is driven until the difference between the first pressure and the second pressure is equal to or more than a predetermined threshold so as to move the end of the pipette tip 170 to the bottom surface (reference portion 180) side of the flow path 60, and the step of measuring the second pressure inside the pipette tip 170 by the air pressure sensor 131 is repeated. Subsequently, the control unit 160 determines that the end of the pipette tip 170 is in the vicinity of the reference portion 180 base on the difference caused between the first pressure and the second pressure, and detects the end height of the pipette tip 170 with respect to the reference portion 180. That is, the control unit 160 detects the air pressure by the air pressure sensor 131 so as to detect the end height of the pipette tip 170 with respect to the reference portion 180.

In the step (step S120) of detecting the end height of the pipette tip 170, it is allowable to measure the air pressure within the pipette tip 170 by the air pressure sensor 131 while air is continuously or intermittently discharged from the end of the pipette tip 170 and the end of the pipette tip 170 is brought close to the reference portion 180. In this case, the air pressure before moving the pipette tip 170 is determined as the first pressure. The air pressure in the pipette tip 170 measured by the air pressure sensor 131 while the end of the pipette tip 170 is brought close to the reference portion 180 is determined as the second pressure. Even in this case, the end height of the pipette tip 170 can be detected with high accuracy.

Next, the reference height of the pipette nozzle 116 is set (step S130). Specifically, the control unit 160 drives the pipette nozzle drive mechanism 112 to move the pipette nozzle 116 from the height (position) of the pipette nozzle 116 when the end of the pipette tip 170 is detected in step S120 to achieve a state in which the end of the pipette tip 170 has a predetermined height from the bottom surface of the flow path 60 at the time of removing a liquid from the inside of the flow path 60. Then, the control unit sets the height of the pipette nozzle 116 when the end of the pipette tip 170 is at a predetermined height (for example, 100 μm) to the reference height of the pipette nozzle 116.

Next, a measurement liquid is injected into the detection chip 10 (step S140). Specifically, the control unit 160 operates the conveyance stage 122, the pipette nozzle drive mechanism 112, and the liquid delivery pump drive mechanism 113 to inject a measurement liquid from the well storing the measurement liquid into the flow path 60 of the detection chip 10 via the pipette tip 170. This step is executed immediately after the reference height of the pipette nozzle is set, and thus, correction of the reference height of the pipette nozzle is not particularly necessary. At this time, in a case where the reaction field on the metal film 30 of the detection chip is protected by the preservation reagent, it is allowable to cause the plunger 115 to reciprocate in a state where the position of the end of the pipette tip 170 is fixed, and repeat aspiration and discharge of the measurement liquid (washing liquid) with the pipette tip 170 to allow the measurement liquid to reciprocate in the flow path 60, so as to wash away the preservation reagent. In this case, the measurement liquid used for washing is sucked and removed by the pipette tip 170, and a new measurement liquid is again injected into the flow path 60 of the detection chip 10.

Next, the incident angle of the excitation light α is determined (step S150). The control unit 160 operates the conveyance stage 122 to move the detection chip 10 to the detection position. The control unit 160 drives the angle adjustment mechanism 142 to scan the incident angle of the excitation light α, and at the same time, drives the sensor control unit 153 to detect the plasmon scattered light γ by the light receiving sensor 157. Then, the angle maximizing the light amount of the plasmon scattered light γ is determined as the incident angle (enhancement angle) of the excitation light α. Next, the measurement liquid is aspirated into the pipette tip 170 to remove the measurement liquid from the inside of the flow path 60.

Next, the measurement liquid is sucked and removed from the flow path 60 (step S160). At this time, the control unit 160 obtains the correction amount of the height of the pipette nozzle 116 from the reference height so as to cancel out the variation of the end height of the pipette tip 170 by any one of the above-described means. Then, the control unit 160 moves the height of the pipette nozzle 116 to the corrected reference height via the pipette nozzle drive mechanism 112. The control unit 160 operates the liquid delivery pump drive mechanism 113 to suck and remove the measurement liquid in the flow path 60 into the pipette tip 170. As the reference height of the pipette nozzle is corrected and the end position of the pipette tip 170 is managed with high accuracy, it is possible to reduce the residual liquid amount of the measurement liquid in the flow path 60 and manage the amount to a constant amount, leading to achievement, in the subsequent primary reaction step, of reducing the proportion of dilution of the specimen by the residual liquid and achievement of management with a constant dilution ratio.

Subsequently, the detection target substance in the specimen is reacted with the primary antibody (primary reaction; step S170). The control unit 160 operates the conveyance stage 122, the pipette nozzle drive mechanism 112, and the liquid delivery pump drive mechanism 113 to inject a primary reaction solution (specimen, or specimen diluent) from the well storing the primary reaction solution into the flow path 60 of the detection chip 10 via the pipette tip 170, and allows the plunger 115 to reciprocate to perform reciprocating liquid delivery for a certain period of time. In a case where a detection target substance is present in the specimen, at least a portion of the detection target substance binds to the primary antibody. After the primary reaction, the primary reaction solution is aspirated into the pipette tip 170 to remove the specimen from the flow path 60.

Note that the types of the specimen and the detection target substance are not particularly limited. Examples of specimens include body fluids such as blood, serum, plasma, urine, nostrils, saliva, and semen, and diluents thereof. Examples of the detection target substance include nucleic acids (DNA, RNA, or the like), proteins (polypeptides, oligopeptides, or the like), amino acids, carbohydrates, lipids and modified molecules thereof.

Next, the metal film 30 is washed with a washing liquid such as a buffer solution (step S180). The control unit 160 operates the conveyance stage 122, the pipette nozzle drive mechanism 112, and the liquid delivery pump drive mechanism 113 to inject a washing liquid from the well storing the washing liquid into the flow path 60 of the detection chip 10 via the pipette tip 170, and allows the plunger 115 to reciprocate to perform reciprocating liquid delivery for a certain period of time. Next, the washing liquid containing the residual primary reaction solution is removed from the flow path 60.

Similarly to the step (step S160) of removing the measurement liquid, the control unit 160 obtains, in this step of removing the washing liquid, the correction amount of the height of the pipette nozzle 116 from the reference height so as to cancel out the variation of the end height of the pipette tip 170 by any one of the above-described means. Then, the control unit 160 moves the height of the pipette nozzle 116 to the corrected reference height via the pipette nozzle drive mechanism 112. Then, the control unit 160 moves the height of the pipette nozzle 116 to the corrected reference height via the pipette nozzle drive mechanism 112, and removes the washing liquid containing the residual primary reaction solution from the flow path 60 at the corrected position. As the reference height of the pipette nozzle 116 is corrected and the end position of the pipette tip 170 is managed with high accuracy, it is possible to reduce the residual liquid amount of the primary reaction solution in the flow path 60, leading to the prevention, in the subsequent steps, of the specimen from being further captured by the primary reaction solution remaining as the residual liquid. In addition, managing the primary reaction time makes it possible to detect the concentration of the specimen with high accuracy.

Subsequently, the detection target substance captured on the metal film 30 is labeled with a fluorescent substance (secondary reaction; step S190). Specifically, the control unit 160 operates the conveyance stage 122, the pipette nozzle drive mechanism 112, and the liquid delivery pump drive mechanism 113 to inject secondary reaction solution (labeling antibody solution) from the well storing the secondary reaction solution into the flow path 60 of the detection chip 10 via the pipette tip 170, and allows the plunger 115 to reciprocate to perform reciprocating liquid delivery for a certain period of time. In the flow path 60, a detection target substance captured on the metal film 30 is labeled with a fluorescent substance by an antigen-antibody reaction. After the secondary reaction, the secondary reaction solution is aspirated into the pipette tip 170 to remove the specimen from the flow path 60.

Next, the metal film 30 is washed with a washing liquid such as a buffer solution (step S200). The control unit 160 operates the conveyance stage 122, the pipette nozzle drive mechanism 112, and the liquid delivery pump drive mechanism 113 to inject a washing liquid from the well storing the washing liquid into the flow path 60 of the detection chip 10 via the pipette tip 170, and allows the plunger 115 to reciprocate to perform reciprocating liquid delivery for a certain period of time. Next, the washing liquid containing the residual secondary reaction solution is removed from the flow path 60.

Similarly to the step (step S160) of removing the measurement liquid and the washing step (S180) after the primary reaction, the control unit 160 obtains, in this step of removing the washing liquid, the correction amount of the height of the pipette nozzle 116 from the reference height so as to cancel out the variation of the end height of the pipette tip 170 by any one of the above-described means of the present invention. Then, the control unit 160 moves the height of the pipette nozzle 116 to the corrected reference height via the pipette nozzle drive mechanism 112. Then, the control unit 160 moves the height of the pipette nozzle 116 to the corrected reference height via the pipette nozzle drive mechanism 112, and removes the washing liquid containing the residual secondary reaction solution from the flow path 60 at the corrected position. As the reference height of the pipette nozzle 116 is corrected and the end position of the pipette tip 170 is managed with high accuracy, it is possible to reduce the residual liquid amount of the secondary reaction solution in the flow path 60, leading to the prevention, in the subsequent steps of detecting a detection target substance, of light emission from an un-reacted fluorescent substance toward the residual detection target substance as a remaining liquid. Consequently, it is possible to detect the concentration of the specimen with high accuracy.

The order of the primary reaction (step S170) and the secondary reaction (step S190) is not limited to this. For example, it is allowable to first allow the detection target substance to bind to the secondary antibody and thereafter supply a liquid containing these complexes onto the metal film 30. Moreover, a specimen and a labeling liquid may be simultaneously supplied on the metal film 30.

Next, the detection target substance is detected (step S210). Specifically, the control unit 160 operates the conveyance stage 122 to move the detection chip 10 to the detection position. The control unit 160 subsequently controls the light receiving sensor 157 such that, while driving the light source control unit 143 to apply the excitation light α to a predetermined position of the metal film 30 at the incident angle (enhancement angle) determined in step S120, the sensor control unit 153 is driven to detect the intensity of the fluorescence δ emitted from above the metal film 30 (surface of the metal film 30 and the vicinity thereof).

Note that the control unit 160 may measure a blank value after determining (in step S150) the incident angle (before the primary reaction of S180). In this case, the excitation light α is applied to the metal film 30 at an enhancement angle, and the detection value of the light receiving sensor 157 is set to be a blank value. Then, the blank value is subtracted in the step (step S210) of detecting the detection target substance, from the detection value of fluorescence δ, so as to calculate the amount of fluorescence δ indicating the amount of the detection target substance in the specimen.

Note that the step of correcting the height of the pipette nozzle 116 from the reference height need not be performed in all cases where the liquid is removed from the inside of the flow path 60. In particular, correction of the height of the pipette nozzle 116 from the reference height may be performed in a measurement liquid discharge step (step S160), a washing step following the primary reaction (step S180), and a washing step (step S200) after the secondary reaction, in operation of removing the liquid from the inside of the flow path 60. Moreover, it would be sufficient to perform this correction in the measurement liquid discharge step (step S160) and the washing step (step S200) after the secondary reaction. The step of correcting the height of the pipette nozzle 116 from the reference height in the measurement liquid discharge step (step S160) is performed in order to prevent dilution of the specimen in the primary reaction due to excessive residual measurement liquid in the flow path 60. The step of correcting the height of the pipette nozzle 116 from the reference height in the washing step (step S180) after the primary reaction is performed in order to prevent continuation of the primary reaction after that point due to excessive residual primary reaction solution in the flow path 60. The step of correcting the height of the pipette nozzle 116 from the reference height in the washing step (step S200) after the secondary reaction is performed because the fluorescent substance floating in the labeling liquid remaining in the flow path 60 might make it difficult to distinguish between the substance and the fluorescent substance reacted with the detection target substance, leading to generation of noise.

Since the residual liquid in the washing step (step S180) after the primary reaction has a comparatively small influence, it is possible to omit the correction from the reference height in this step. Additionally, in the discharge step (step S160) of the measurement liquid, the elapsed time after setting the reference height in the first process is comparatively short and the temperature change of the pipette tip 170 is comparatively small. Accordingly, it is also possible to omit the correction from the reference height, in this step. Since the elapsed time after the detection of the end height of the pipette tip 170 is long in the washing step (step S200) after the secondary reaction, the change amount in the length of the pipette tip 170 is the largest, making it possible to achieve a great effect of correcting the reference height, having the greatest significance.

Figure 9:
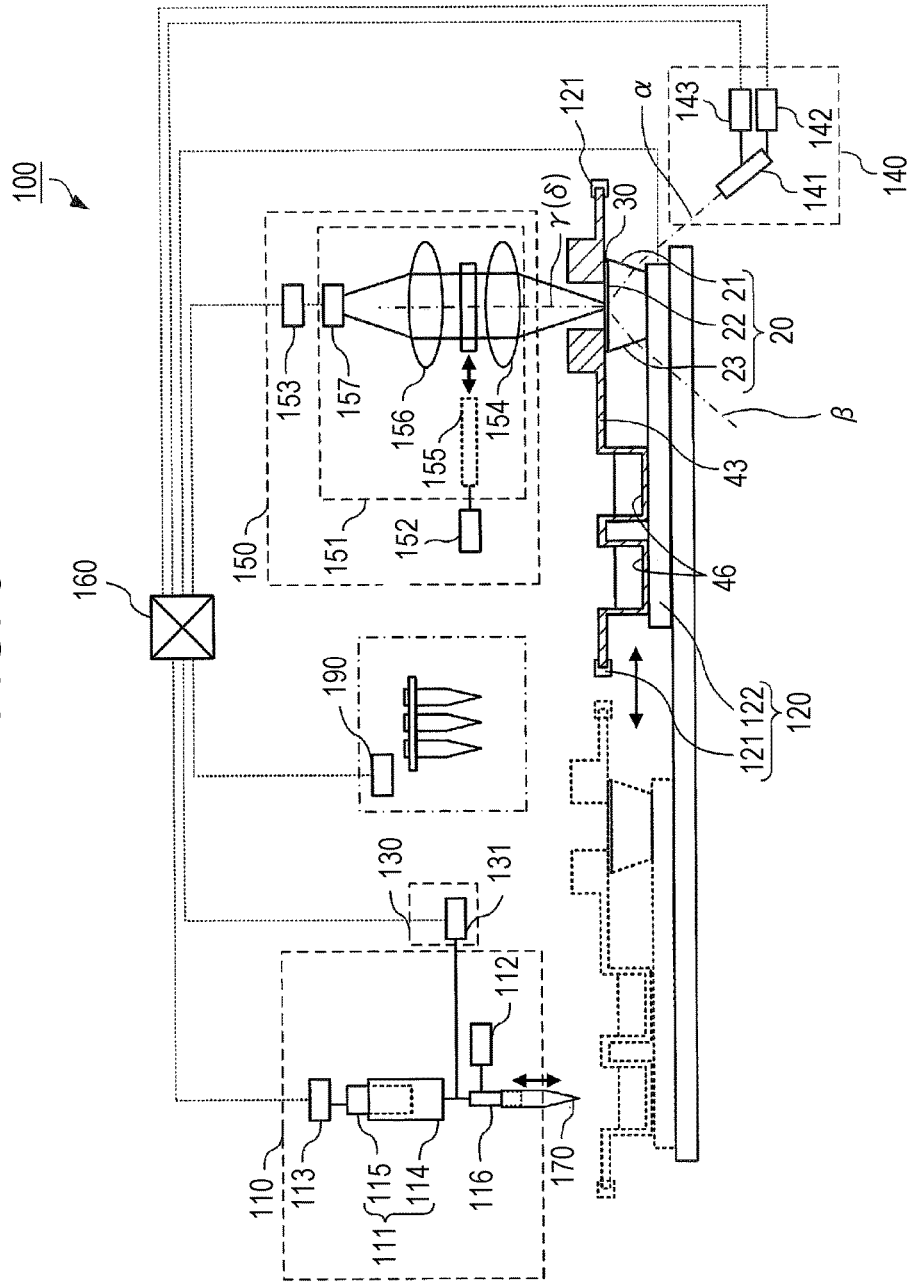
FIG. 9 is a diagram illustrating a configuration around a pipette tip of an SPFS apparatus.

Moreover, as illustrated in FIG. 9, the SPFS apparatus may further include a first temperature measurement means 190 for measuring the temperature of the attachment space. The first temperature measurement means 190 is not particularly limited as long as it can measure the internal temperature around the attached pipette tip 170. An example of the first temperature measurement means 190 is a temperature sensor. Since an estimated value of the difference between the maximum temperature and the minimum temperature of the pipette tip 170 in the reaction step can be estimated by the first temperature measurement means 190 with higher accuracy, it is possible to correct the height of the pipette nozzle 116 from the reference height with high accuracy.

Second Configuration of SPFS Apparatus

FIG. 10 is a schematic diagram illustrating a configuration around a pipette tip of a surface plasmon-field enhanced fluorescence analyzer (SPFS apparatus) an example of an apparatus for performing the reaction method according to a second embodiment. FIGS. 10A and 10B are a side view and a cross-sectional view, respectively, illustrating arrangement of a second temperature measurement means 192, and FIGS. 10C and 10D are a side view and a cross-sectional view, respectively, illustrating arrangement of the second temperature measurement means 192 and arrangement of a temperature adjustment mechanism 194.

Figure 10A:
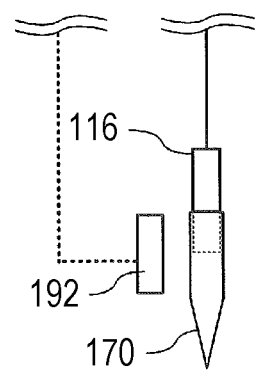
FIGS. 10A and 10B are a side view and a cross-sectional view, respectively, illustrating arrangement of a second temperature measurement means.
Figure 10B:

As illustrated in FIGS. 10A and 10B, the SPFS apparatus capable of performing the reaction method according to the second embodiment includes the second temperature measurement means 192.

The second temperature measurement means 192 measures the temperature of the pipette tip 170. The second temperature measurement means 192 is not particularly limited as long as it can achieve the above-described function. Examples of the second temperature measurement means 192 include thermocouples, servomotors, and bolometers. In particular, it is preferable that the second temperature measurement means 192 is a servo mobile because of its capability of performing non-contact measurement of the temperature of the pipette tip 170 in a short time with less cost.

Figure 10C:
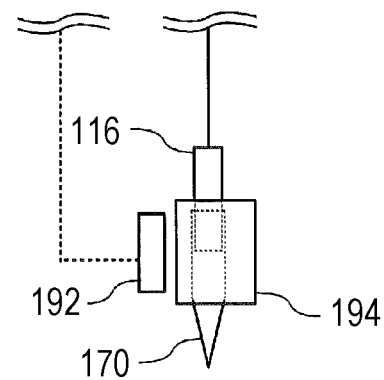
FIGS. 10C and 10D are a side view and a cross-sectional view, respectively, illustrating arrangement of the second temperature measurement means and arrangement of a temperature adjustment mechanism.
Figure 10D:
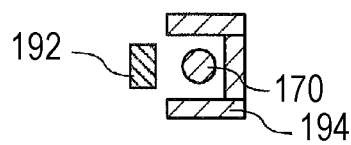

Moreover, the SPFS apparatus may include the temperature adjustment mechanism 194 that adjusts the temperature of the pipette tip 170. The temperature adjustment mechanism 194 is not particularly limited as long as it can achieve the above-described function. An example of the temperature adjustment mechanism 194 is a temperature control block. In this case, as illustrated in FIGS. 10C and 10D, the temperature adjustment mechanism 194 is arranged at a height excluding portions at which the end of the pipette tip 170 is inserted into the detection chip 10' and the well 60, and at a position excluding the second temperature measurement means 192.

The control unit 160 activates the temperature adjustment mechanism 194 to adjust the temperature of the pipette tip 170 for a duration from completion of the first process with the pipette tip 170 being attached to the pipette nozzle 116 until finish of the reaction step.

This application claims priority based on Japanese Patent Application No. 2015-223436 filed on Nov. 13, 2015. The contents described in the application specification and drawings are all incorporated herein by reference.

INDUSTRIAL APPLICABILITY

The reaction method according to the present invention is capable of measuring the detection target substance with high reliability, for example. Accordingly, the reaction method according to the present invention is expected to contribute to the development, growth and expansion of a very simple quantitative immunoassay system.

REFERENCE SIGNS LIST 10, 10' Detection chip
20 Prism
21 Incident surface
22 Film forming surface
23 Emission surface
30 Metal film
40 Flow path lid
41 Reaction region
42 Reagent storage region
43 Flow path groove
44 First through hole
45 Second through hole
46 Recess
60 Flow path
60' Well
70 Injection portion
80 Reservoir
100 SPFS apparatus
110 Liquid delivery unit
111 Pipette
112 Pipette moving unit
113 Liquid delivery pump moving mechanism
114 Syringe
115 Plunger
116 Pipette nozzle
120 Conveyance unit
121 Chip holder
122 Conveyance stage
130 Position information acquisition unit
131 Air pressure sensor
140 Light emitting unit
141 Light source unit
142 Angle adjustment mechanism
143 Light source control unit
150 Photodetector
151 Light receiving unit
152 Position switching mechanism
153 Sensor control unit
154 First lens
155 Optical filter
156 Second lens
157 Light receiving sensor
160 Control unit
170 Pipette tip
180 Reference portion
190 First temperature measurement means
192 Second temperature measurement means
194 Temperature adjustment mechanism
A Pipette tip
B Pipette nozzle
C Reference portion
α Excitation light
β Reflected light
γ Plasmon scattered light
δ Fluorescence

The invention claimed is:

1. A reaction method comprising reacting two or more substances with each other by using a pipette tip, attached to a pipette nozzle, for sucking or discharging a liquid to supply a liquid to a reaction field and remove the liquid from the reaction field a plurality of times, the reaction method further comprising:

prior to the reacting, detecting an end height of the pipette tip and setting a reference height of the pipette nozzle based on the end height of the pipette tip; and correcting, in a course of the reaction step, the height of the pipette nozzle from the reference height so as to cancel out variation in the end height of the pipette tip due to a change in the temperature of the pipette tip.

2. The reaction method according to claim 1, wherein the correcting includes correcting the height of the pipette nozzle from the reference height so as to make the height of the pipette nozzle higher with respect to the reaction field.

3. The reaction method according to claim 1, wherein the second process includes correcting includes correcting the height of the pipette nozzle from the reference height in accordance with an elapsed time of the reaction step reacting.

4. The reaction method according to claim 3, wherein the correcting includes
estimating a variation of the end height of the pipette tip based on:
a length of the pipette tip between an end and a portion fitting with the pipette nozzle;
a linear expansion coefficient of the pipette tip;
a variation of a temperature of the pipette tip with time; and
an elapsed time of the reacting, and
correcting the height of the pipette nozzle from the reference height based on the estimated variation.

5. The reaction method according to claim 4, wherein a variation rate of the end height of the pipette tip decreases with time.

6. The reaction method according to claim 4, wherein the detecting further includes measuring a temperature around the pipette tip when the pipette tip is attached to the pipette nozzle by a first temperature measurement means measurer, and correcting the height of the pipette nozzle from the reference height in accordance with a maximum change amount of the temperature of the pipette tip estimated based on a measured value.

7. The reaction method according to claim 4, wherein the detecting further includes measuring a temperature of the pipette tip by a second temperature measurement means measurer, and correcting the height of the pipette nozzle from the reference height in accordance with a maximum change amount of the temperature of the pipette tip estimated based on the measured value.

8. The reaction method according to claim 1, wherein
the detecting further includes measuring a temperature of the pipette tip by a second temperature measurer, and
the correcting further includes measuring the temperature of the pipette tip by the second temperature measurer, as well as correcting the height of the pipette nozzle from the reference height in accordance with a difference between the temperature of the pipette tip measured by the second temperature measurer in the detecting at a time when the end height of the pipette tip is detected and the temperature of the pipette tip measured by the second temperature measurer in the reacting.

9. The reaction method according to claim 8, wherein the correcting includes correcting the reference height of the pipette nozzle based on:
a length of the pipette tip between an end and a portion fitting with the pipette nozzle;
a linear expansion coefficient of the pipette tip; and
a difference between the temperature of the pipette tip further measured by the second temperature measurer, the temperature of the pipette tip being the temperature at the time when the end height of the pipette tip is detected, measured by the second temperature measurer in the detecting and the temperature of the pipette tip measured by the second temperature measurer in the reacting.

10. The reaction method according to claim 1, wherein the pipette tip is formed of resin, and
a linear expansion coefficient of the pipette tip is 5.8× $10^{-5}$/° C. or more.

11. The reaction method according to claim 1, wherein a temperature of the pipette tip is adjusted by a temperature adjuster.

12. The reaction method according to claim 1, wherein the correcting is performed after the liquid is supplied to the reaction field and before the liquid is removed from the reaction field.

13. The reaction method according to claim 1, wherein
the reaction field is arranged at a bottom surface of a flow path or at a bottom surface of a well, capable of storing a liquid, and
the reacting includes an immune reaction in the reaction field.

14. The reaction method according to claim 2, wherein the correcting includes correcting the height of the pipette nozzle from the reference height in accordance with an elapsed time of the reacting.

15. The reaction method according to claim 2, wherein
the detecting further includes measuring a temperature of the pipette tip by a second temperature measurer, and
the correcting further includes measuring the temperature of the pipette tip by the second temperature measurer, as well as correcting the height of the pipette nozzle from the reference height in accordance with a difference between the temperature of the pipette tip measured by the second temperature measurer in the detecting at a time when the end height of the pipette tip is detected and the temperature of the pipette tip measured by the second temperature measurer in the reacting.

16. The reaction method according to claim 2, wherein
the pipette tip is formed of resin, and
a linear expansion coefficient of the pipette tip is 5.8× $10^{-5}$/° C. or more.

17. The reaction method according to claim 2, wherein a temperature of the pipette tip is adjusted by a temperature adjuster.

18. The reaction method according to claim 2, wherein the correcting is performed after the liquid is supplied to the reaction field and before the liquid is removed from the reaction field.

19. The reaction method according to claim 2, wherein
the reaction field is arranged at a bottom surface of a flow path or at a bottom surface of a well, capable of storing a liquid, and
the reacting includes an immune reaction in the reaction field.

20. The reaction method according to claim 3, wherein
the detecting further includes measuring a temperature of the pipette tip by a second temperature measurer, and
the correcting further includes measuring the temperature of the pipette tip by the second temperature measurer, as well as correcting the height of the pipette nozzle from the reference height in accordance with a difference between the temperature of the pipette tip measured by the second temperature measurer in the detecting at a time when the end height of the pipette tip is detected and the temperature of the pipette tip measured by the second temperature measurer in the reacting.

* * * * *